(12) United States Patent  (10) Patent No.: US 9,168,374 B2
Su  (45) Date of Patent: Oct. 27, 2015

(54) INTRA-BURST PULSE VARIATION FOR STIMULATION THERAPY

(75) Inventor: Xin Su, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/358,038

(22) Filed: Jan. 25, 2012

(65) Prior Publication Data

US 2012/0197336 A1 Aug. 2, 2012

Related U.S. Application Data

(60) Provisional application No. 61/437,448, filed on Jan. 28, 2011.

(51) Int. Cl.
*A61N 1/18* (2006.01)
*A61N 1/36* (2006.01)

(52) U.S. Cl.
CPC ........ *A61N 1/36007* (2013.01); *A61N 1/36107* (2013.01); *A61N 1/36171* (2013.01); *A61N 1/36178* (2013.01)

(58) Field of Classification Search
USPC ................ 607/2, 9, 11, 12, 15, 39, 40, 46, 48
See application file for complete search history.

(56) References Cited

U.S. PATENT DOCUMENTS

| | | | |
|---|---|---|---|
| 4,607,639 A * | 8/1986 | Tanagho et al. ................. | 607/40 |
| 5,723,001 A * | 3/1998 | Pilla et al. ........................ | 607/68 |
| 6,466,822 B1 * | 10/2002 | Pless .............................. | 607/45 |
| 6,990,376 B2 | 1/2006 | Tanagho et al. | |
| 7,047,078 B2 | 5/2006 | Boggs et al. | |
| 7,050,856 B2 | 5/2006 | Stypulkowski | |
| 7,117,034 B2 | 10/2006 | Kronberg | |
| 7,174,213 B2 * | 2/2007 | Pless .............................. | 607/45 |
| 7,333,858 B2 * | 2/2008 | Killian et al. ................... | 607/56 |
| 7,623,925 B2 | 11/2009 | Grill et al. | |
| 7,643,880 B2 | 1/2010 | Tanagho et al. | |
| 7,734,340 B2 | 6/2010 | De Ridder | |
| 8,265,771 B2 * | 9/2012 | Donofrio et al. ................ | 607/61 |
| 8,301,263 B2 * | 10/2012 | Donofrio et al. ................ | 607/60 |
| 2004/0147976 A1 | 7/2004 | Gordon et al. | |
| 2006/0190047 A1 * | 8/2006 | Gerber et al. ................... | 607/41 |
| 2008/0125825 A1 * | 5/2008 | Ben-Ezra et al. ............... | 607/14 |
| 2009/0036945 A1 | 2/2009 | Chancellor et al. | |
| 2009/0222058 A1 | 9/2009 | Craggs | |

(Continued)

OTHER PUBLICATIONS

Boggs et al. Frequency Dependent Selection of Reflexed by Pudendal Afferents in the Cat, J Physiol 577,1 (2006) pp. 115-126.*

(Continued)

*Primary Examiner* — Brian T Gedeon
(74) *Attorney, Agent, or Firm* — Shumaker & Sieffert, P.A.

(57) ABSTRACT

In general, the disclosure is directed to devices, systems, and techniques for delivering electrical stimulation to a patient with varying pulse frequencies within each burst of pulses. The pulse frequency variation within each burst of pulses may be between approximately 20 Hz and 40 Hz. In some examples, the pulse frequency may be increased, decreased, or polynomially varied within each burst. In other examples, the frequency of intrinsic nerve impulses may be detected and used to deliver pulses with the detected frequency or an inverse of the detected frequency. Electrical stimulation therapy with intra-burst pulse frequency variation may alleviate bladder dysfunction, bowel dysfunction, pain or other disorders.

29 Claims, 8 Drawing Sheets

(56) References Cited

U.S. PATENT DOCUMENTS

2010/0114200 A1* 5/2010 Krause et al. .................. 607/4
2011/0184488 A1* 7/2011 De Ridder ..................... 607/46

OTHER PUBLICATIONS

"Unilateral Conditional Dorsal Genital Nerve Stimulation to Suppress Neurogenic Detrusor Overactivity Using a Needle Electrode," International Continence Society Abstract, 39th Annual Meeting of the ICS, San Francisco, CA, USA, Sep. 29th through Oct. 3rd, 2009, 2 pp.

Amir et al., "Burst Discharge in Primary Sensory Neurons: Triggered by Subthreshold Oscillations, Maintained by Depolorizing Afterpotentials," The Journal of Neuroscience, vol. 22(3), Feb. 2002, 12 pp.

Bruns et al., "Intraurethral Stimulation for Reflex Bladder Activation Depends on Stimulation Pattern and Location," Neurourology and Urodynamics, Aug. 2009, pp. 561-566.

Su et al., "Effects of Opiods on Mechanosensitive Pelvic Nerve Afferent Fibers Innervating the Urinary Bladder of the Rat, " Journal of Neurophisiology, vol. 77, Mar. 1997, pp. 1566-1580.

Su et al., "Mechanosensitive Pelvic Nerve Afferent Fibers Innervating the Colon of the Rat Are Polymodal in Character," Journal of Neurophysiology, vol. 80, Nov. 1998, pp. 2632-2644.

Su et al., "The Effect of Amitriptyline on Ectopic Discharge of Primary Afferent Fibers in the L5 Dorsal Root in a Rat Model of Neuropathic Pain," Anesthesia & Analgesia, vol. 108(5), May 2009, 9 pp.

* cited by examiner

INTRA-BURST PULSE VARIATION FOR STIMULATION THERAPY

This application claims the benefit of U.S. Provisional Application No. 61/437,448, to Su, filed Jan. 28, 2011, and entitled "INTRA-BURST PULSE VARIATION FOR STIMULATION THERAPY," which is incorporated herein by reference in its entirety.

TECHNICAL FIELD

The disclosure relates to implantable medical devices and, more particularly, medical devices that deliver electrical stimulation to a patient.

BACKGROUND

Bladder dysfunction, such as overactive bladder, urgency, or urinary incontinence, and bowel dysfunction, such as problems with frequency, consistency and/or the ability to control bowel movements and pelvic pain, are problems that may afflict people of all ages, genders, and races. Various muscles, nerves, organs and conduits within the pelvic floor cooperate to maintain the normal functions. A variety of disorders may compromise performance of one or more organs in the pelvic area and contribute to diseases such as an overactive bladder, urgency, urinary or fecal incontinence, or chronic pelvic pain. Many of the disorders may be associated with aging, injury or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence.

Urinary retention generally refers to an inability to empty the bladder and can be caused by nerve problems that interfere with signals between the brain and bladder. If the nerves are not working properly, the brain may not receive a message that the bladder is full and requires voiding of urine. Even if a patient knows that the bladder is full, the bladder muscle that contracts to expel urine may not be activated, or the urethral sphincter muscles may not relax.

Pelvic pain generally refers to pain in the pelvic region and can be a symptom of another disease. Spasms or tension of pelvic floor muscle, irritable bowel syndrome, interstitial cystitis and many others can cause pelvic pain. Long lasting pain can develop into chronic pelvic pain possibly caused from the sensitization of the central nervous system.

SUMMARY

In general, the disclosure is directed to techniques for delivering electrical stimulation to a patient in bursts, with varying pulse frequencies within each burst of pulses. The pulse frequency within each burst of pulses (i.e., the intra-burst pulse frequency variation) may vary between approximately 1 Hz and 100 Hz, and more specifically, between 20 Hz and 40 Hz. In some examples, the pulse frequency may be increased, decreased, or polynomially varied within each burst according to a pulse variation profile. In other examples, the frequency of intrinsic nerve impulses may be detected and used to deliver pulses with a detected frequency variation profile or an inverse of the detected frequency variation profile. Electrical stimulation therapy with intra-burst pulse frequency variation may at least partially alleviate bladder dysfunction, bowel dysfunction, pelvic pain or other disorders.

In one aspect, the disclosure is directed to a method that includes delivering electrical stimulation therapy to a patient, wherein the electrical stimulation therapy comprises a plurality of bursts and a plurality of pulses within each of the plurality of bursts, and varying, by a control module, a pulse frequency of the plurality of pulses within each of the plurality of bursts, wherein the pulse frequency is varied between approximately 20 Hz and 40 Hz.

In another aspect, the disclosure is directed to a system that includes a therapy delivery module configured to generate and deliver electrical stimulation therapy to a patient, wherein the electrical stimulation therapy comprises a plurality of bursts and a plurality of pulses within each of the plurality of bursts. The system also includes a control module configured to vary a pulse frequency of the plurality of pulses within each of the plurality of bursts, wherein the pulse frequency is varied between approximately 20 Hz and 40 Hz.

In a further aspect, the disclosure is directed to a system that includes means for delivering electrical stimulation therapy to a patient, wherein the electrical stimulation therapy comprises a plurality of bursts and a plurality of pulses within each of the plurality of bursts. The system also includes means for varying a pulse frequency of the plurality of pulses within each of the plurality of bursts, wherein the pulse frequency is varied between approximately 20 Hz and 40 Hz.

In a further aspect, the disclosure is directed to a method that includes detecting a frequency variation of intrinsic nerve impulses within a burst of impulses, determining an inverse pulse frequency variation based on the frequency variation of intrinsic nerve impulses, and delivering electrical stimulation therapy to a patient, wherein the electrical stimulation therapy comprises one or more bursts of pulses at least partially defined by the inverse pulse frequency variation.

In a further aspect, the disclosure is directed to a system that includes an impulse sensing module configured to detect a frequency variation of intrinsic nerve impulses within a burst of impulses, a control module configured to determine an inverse pulse frequency variation based on the frequency variation of intrinsic nerve impulses, and a therapy delivery module configured to deliver electrical stimulation therapy to a patient, wherein the control module at least partially defines one or more bursts of pulses of the electrical stimulation therapy by the inverse pulse frequency variation.

In a further aspect, the disclosure is directed to a system that includes means for detecting a frequency variation of intrinsic nerve impulses within a burst of impulses, means for determining an inverse pulse frequency variation based on the frequency variation of intrinsic nerve impulses, and means for delivering electrical stimulation therapy to a patient, wherein the electrical stimulation therapy comprises one or more bursts of pulses at least partially defined by the inverse pulse frequency variation.

The details of one or more example are set forth in the accompanying drawings and the description below. Other features, objects, and advantages will be apparent from the description and drawings, and from the claims.

DETAILED DESCRIPTION

Figure 1:
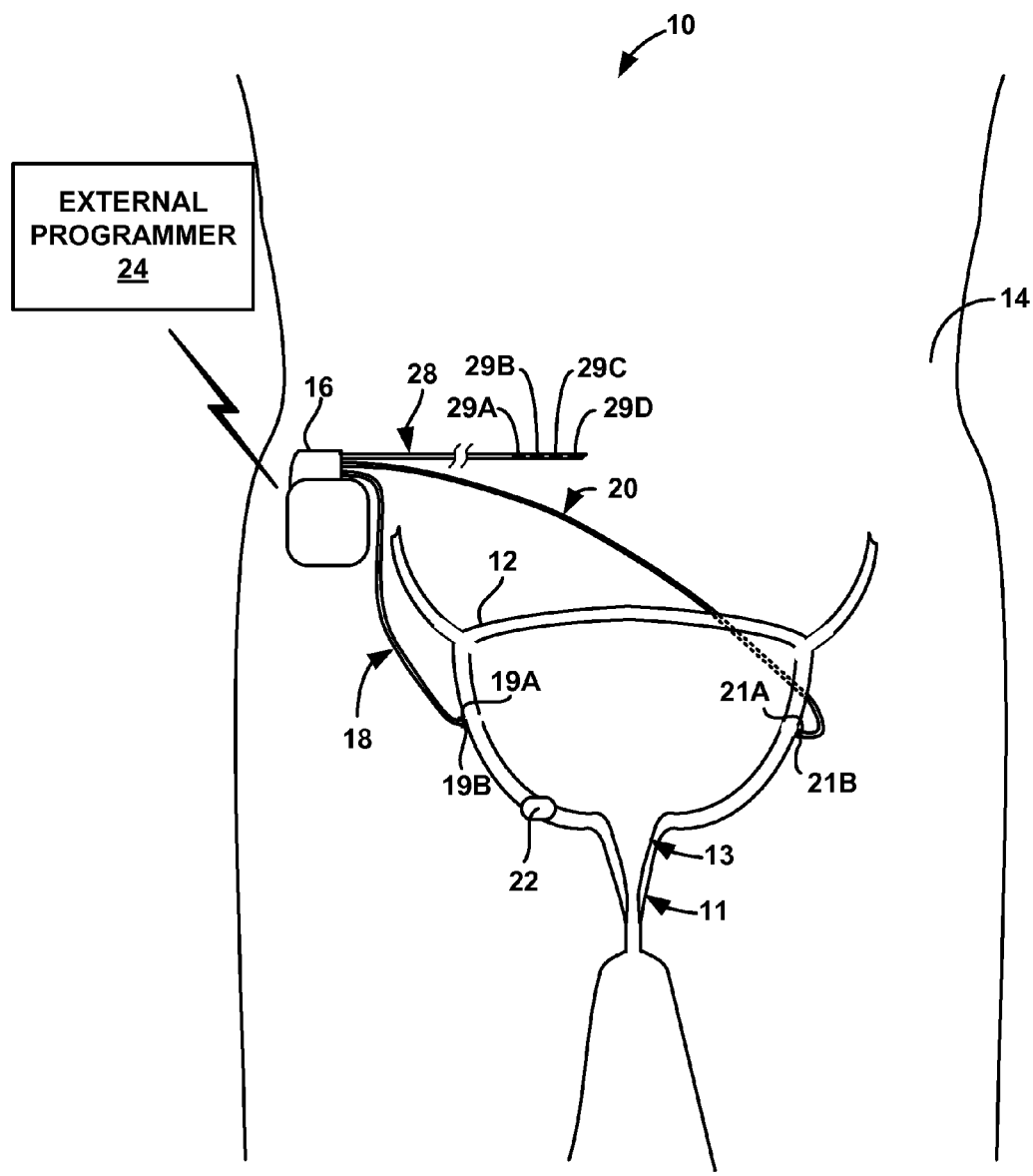
FIG. 1 is a conceptual diagram illustrating an example system that delivers electrical stimulation to a patient to manage a bladder dysfunction, such as an overactive bladder, urgency, or urinary incontinence after termination of the stimulation.

Bladder dysfunction refers to a condition of improper functioning of the bladder or urinary tract, and may include, for example, an overactive bladder, urgency, pain or urinary incontinence. Urgency is a sudden, compelling urge to urinate, and may often, though not always, be associated with urinary incontinence. Urinary incontinence refers to a condition of involuntary loss of urine, and may include urge incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence. These types of disorder may occur when the response of bladder afferent nerves to bladder distension is enhanced.

Another type of bladder dysfunction, urinary retention, generally refers to an inability to empty the bladder and can be caused by nerve problems that interfere with signals between the brain and bladder. If the nerves are not working properly, the brain may not receive a message that the bladder is full and requires voiding of urine. Even if a patient knows that the bladder is full, the bladder muscle that contracts to expel urine may not be activated, or the urethral sphincter muscles may not relax.

One type of therapy for treating bladder dysfunction includes delivery of electrical stimulation to a target tissue site within a patient. This electrical stimulation may cause a therapeutic effect, e.g., a beneficial physiological response, during delivery of the electrical stimulation. For example, delivery of electrical stimulation from an implantable medical device (IMD) to a spinal nerve, a sacral nerve, a pudendal nerve, dorsal genital nerve, a tibial nerve, an inferior rectal nerve, a perineal nerve, or branches of any of the aforementioned nerves may provide an immediate therapeutic effect for bladder dysfunction, such as a physiological response of a reduction in the frequency of bladder contractions, e.g., for overactive bladder, urgency, pain, or urinary incontinence. Electrical stimulation of the sacral nerve may modulate afferent nerve activities to restore urinary function during the electrical stimulation. Also, electrical stimulation may be delivered to cause relaxation of urethral sphincter muscles and/or contraction of bladder muscles to permit voiding of urine, e.g., in the case of urinary retention.

Clinically efficacious electrical stimulation therapy may be delivered to treat one or more of urine retention, bladder urgency, and pain. Changes in mean frequency of nerve fiber discharge may be used to measure never mediated physiological and pathological effects. However, the temporal pattern of nerve fiber discharge may be more important in neurotransmission. In some examples, techniques described in this disclosure may deliver electrical stimulation with patterned bursts of pulses. The burst patterns may be selected, in some examples, to mimic the properties of nerve firings, and may produce enhanced afferent signals to trigger bladder contractions.

The techniques described in this disclosure, in some examples, are directed to delivering electrical stimulation with burst patterns characterized by varying pulse frequencies within each burst of pulses. In other words, electrical stimulation may be delivered in bursts of pulses, and the frequency of the pulses (i.e., pulse rate) is not constant within each burst. Physiologically, intrinsic nerve impulses have been sometimes observed as being produced in bursts. Electrical stimulation therapy that includes the delivery of bursts of pulses, as opposed to continuous pulses, may be configured, in some examples, to mimic such nerve impulses, and provide an effective therapy for stimulation of nerves, muscles, or other tissues of a patient, e.g., to alleviate bladder urgency and/or urinary retention. In addition, intrinsic nerve impulses have been observed as varying in frequency within each of these bursts. Electrical stimulation therapy may also include burst patterns with a pulse frequency variation within each burst of pulses (i.e., an intra-burst pulse frequency variation). The delivery of bursts of electrical stimulation pulses with varying pulse frequency may, in some cases, mimic or partially mimic one or more characteristics of the intrinsic nerve pulses, such as intra-burst pulse frequency variation characteristics.

In some examples, the intra-burst pulse frequency variation may be between approximately 20 Hz and 40 Hz. Generally; all pulse frequencies within the burst may be within the 20 Hz to 40 Hz range even though they are varied in pulse frequency. This means that pulses within a burst may be delivered at a frequency of 20 to 40 Hz, with variation of the pulse frequency within the burst, e.g., according to a frequency variation profile. However, in other examples, only a subset of the pulses within the burst may fall within the 20 Hz to 40 Hz range. In addition, the frequency of bursts (i.e., an inter-burst frequency) may be between approximately 1 Hz and 10 Hz. This means that bursts may be delivered, in some examples, at a frequency of approximately 1 to 10 bursts per second.

Generally, the intra-burst pulse frequency may increase or decrease over time according to an intra-burst pulse frequency variation profile. In other words, within the burst, the variation of the pulse frequency over time may correspond to a certain profile. In other words, the profile may characterize the rate of change variation of the intra-burst pulse frequencies. In some examples, the pulse frequency of pulses within a given burst may be increased, decreased, or polynomially varied according to a pulse variation profile. In one example, the profile of the intra-burst pulse frequency variation may be linear such that the intra-burst pulse frequency varies linearly or substantially linearly over time. In other examples, the profile may be exponential to continually increase or decrease the rate of change between pulse frequencies. In a further example, the intra-burst pulse frequency variation may have a polynomial profile. A user may set, or the system may determine, a polynomial equation that defines the intra-burst pulse frequency variation. In this manner, the polynomial profile may be used to generate complex variations in intra-burst pulse frequency, e.g., to mimic intrinsic nerve impulse variations. Alternatively, the intra-burst pulse frequency may be varied randomly.

In other examples, the frequency of intrinsic nerve impulses may be detected and used to deliver electrical stimulation therapy. In one example, the detected impulse frequency may be used to deliver stimulation with bursts of pulses having the same or similar intra-burst pulse frequency variations to mimic the intrinsic nerve impulse variations. In an alternative example, the frequency variation of the intrinsic nerve impulses may be used to determine an inverse pulse frequency variation for delivered pulses, e.g., thereby serving to mimic an inverse of the intrinsic nerve impulse variations. This inverse pulse frequency variation may be used to counteract or disrupt the nerve impulses being transmitted within the patient.

Intra-burst pulse frequency variation may be targeted to manage bladder dysfunction, such as an overactive bladder, urgency, or urinary incontinence, or urinary retention. In other examples, the devices, systems, and techniques described in this disclosure may alternatively or additionally be utilized to manage fecal urgency or fecal incontinence (e.g., a colorectal dysfunction), or fecal retention. In some examples, the IMD may implement the techniques described herein to deliver stimulation therapy to at least one nerve (e.g., spinal nerve or a pelvic floor nerve) via at least one electrode electrically connected to the IMD. Bursts with varying pulse frequencies may be used to induce a therapeutic effect relating to the contraction of a detrusor muscle in a patient, e.g., a decrease in frequency of bladder contractions. Reduction in frequency of bladder contractions may reduce urgency of voiding and may reduce urgency and/or urinary incontinence.

As one example, electrical stimulation delivered in bursts with varying pulse frequency variation may be selected to mimic nerve impulses to promote bladder contraction for voiding of urine. Alternatively, or additionally, electrical stimulation delivered in bursts with varying pulse frequency variation may be selected to mimic nerve impulses to increase urethral sphincter pressure to prevent incontinence. As another example, if nerve impulses cause frequent bladder contraction, for example, bursts with the inverse pulse frequency variation may be effective in at least partially neutralizing the nerve impulses to reduce bladder contraction frequency, thereby providing an inhibitory effect quieting bladder activity. In additional examples, electrical stimulation may be delivered with pulse frequency variation selected to promote fecal voiding, e.g., by causing release of the anal sphincter, or avoid fecal incontinence, e.g., by increasing pressure of the anal sphincter.

In incontinence examples, the IMD may deliver stimulation therapy with intra-burst pulse frequency variation prior to, or in response to, detecting a patient parameter indicative of an increased probability of an occurrence of incontinence (e.g., an increased patient activity level). The patient parameter may include, for example, contraction of the urethral or anal sphincter, patient activity level or patient posture state. The IMD may use any suitable sensing mechanism to detect contraction of the urethral or anal sphincter, such as a pressure sensor or an EMG sensor. In addition, the techniques described in this disclosure for varying the pulse frequency within bursts of pulses may be applied to dysfunctions, injuries, or other impairments of other organs, tissues, or nerves. For example, pulse frequency variation may be used to treat bowel dysfunction, pain, inflammation, nerve injury, sexual dysfunction, or other disorders of the pelvic floor and other locations within the patient. Techniques for delivering electrical stimulation in patterned bursts of pulses that mimic the properties of nerve firings in a patient may produce enhanced afferent signals, e.g., to trigger bladder contractions or other physiological responses. In general, delivery of stimulation for alleviation of bladder dysfunction will be described below for purposes of illustration, but without limitation as to other applications of the techniques described in this disclosure.

FIG. 1 is a conceptual diagram illustrating example system 10 that delivers electrical stimulation to patient 14 to manage a bladder dysfunction, such as an overactive bladder, urgency, urinary retention, or urinary incontinence after termination of the stimulation. As described above, electrical stimulation having varying pulse frequencies within each burst of pulses may be delivered to patient 14. In other words, electrical stimulation may be delivered in bursts of pulses, and the frequency of the pulses (i.e., pulse rate) is not constant within each burst. Therefore, electrical stimulation therapy may include a pulse frequency variation within each burst of pulses (i.e., an intra-burst pulse frequency variation). In some examples, the intra-burst pulse frequency variation may be between approximately 20 Hz and 40 Hz. Also, in some examples, the frequency of bursts (i.e., inter-burst frequency) may be between approximately 1 Hz and 10 Hz. The intra-burst pulse frequency may be varied according to a frequency variation profile, such that the pulses vary, for example, by increasing or decreasing in frequency in a least a portion of the burst of pulses as the burst progresses.

In the example of FIG. 1, therapy system 10 includes an implantable medical device (IMD) 16, which is coupled to leads 18, 20, and 28 and sensor 22. System 10 also includes an external programmer 24, which communicates with IMD 16 via wireless communication. IMD 16 generally operates as a therapy device that delivers electrical stimulation to, for example, a target tissue site proximate a spinal nerve, a sacral nerve, a pudendal nerve, dorsal genital nerve, a tibial nerve, an inferior rectal nerve, a perineal nerve, or other pelvic nerves, or branches of any of the aforementioned nerves. IMD 16 provides electrical stimulation to patient 14 by generating and delivering a programmable electrical stimulation signal in the form of electrical pulses to a target a therapy site near lead 28 and, more particularly, near electrodes 29A-29D (collectively referred to as "electrodes 29") disposed proximate to a distal end of lead 28.

IMD 16 may be surgically implanted in patient 14 at any suitable location within patient 14, such as near the pelvis. In some examples, IMD 16 may be implanted in a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via respective lead extensions. Electrical conductors disposed within the lead bodies of leads 18, 20, and 28 electrically connect sense electrodes (e.g., electrodes 19A, 19B, 21A, and 21B) and stimulation electrodes, such as electrodes 29, to a sensing module and a stimulation delivery module (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may increase as the volume of urine within bladder 12 increases. In some examples, system 10 may include electrodes (such as electrodes 19 and 21), a strain gauge, one or more accelerometers, or any other sensor capable of detecting contractions of bladder 12, an electromyogram (EGM) of pelvic floor muscle activity, or any other indication of bladder dysfunction. In other examples, system 10 may not include electrodes 19 and 21 for sensing bladder volume.

One or more medical leads, e.g., leads 18, 20, and 28, may be connected to IMD 16 and surgically or percutaneously tunneled to place one or more electrodes carried by a distal end of the respective lead at a desired nerve or muscle site, e.g., one of the previously listed target therapy sites such as a tissue site proximate a spinal, sacral or pudendal nerve. For example, lead 28 may be positioned such that electrodes 29 deliver an electrical stimulation, such as stimulation with an intra-burst pulse frequency variation, to a spinal, sacral or pudendal nerve to reduce a frequency of contractions of bladder 12. In other examples, lead 28 may also deliver electrical stimulation therapy to different nerves (e.g., a hypogastric nerve, a pudendal nerve, a dorsal penile/clitoral nerve, the urinary sphincter, or any combination thereof) to induce a therapeutic effect such as closure of a urinary sphincter of patient 14. Electrodes 29 of the common lead 28 may deliver stimulation to the same or different nerves. In FIG. 1, leads 18 and 20 are placed proximate to an exterior surface of the wall of bladder 12 at first and second locations, respectively. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 20, 29 of leads 18, 20, 28, respectively may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 18, 20, 28. In some examples, segmented electrodes 29 of lead 28 may be useful for targeting different fibers of the same or different nerves to generate different physiological effects (e.g., therapeutic effects). The intra-burst pulse frequency variation may aid in the capture of different nerves or muscle fibers that react to varying frequencies of stimulation. In examples, one or more of leads 18, 20, 28 may be, at least in part, paddle-shaped (e.g., a "paddle" lead), and may include an array of electrodes on a common surface, which may or may not be substantially flat.

In some examples, one or more of electrodes 19, 20, 29 may be cuff electrodes that are configured to extend at least partially around a nerve (e.g., extend axially around an outer surface of a nerve). Delivering electrical stimulation via one or more cuff electrodes and/or segmented electrodes may help achieve a more uniform electrical field or activation field distribution relative to the nerve, which may help minimize discomfort to patient 14 that results from the delivery of electrical stimulation. An electrical field may define the volume of tissue that is affected when the electrodes 19, 20, 29 are activated. An activation field represents the neurons that will be activated by the electrical field in the neural tissue proximate to the activated electrodes.

The illustrated numbers and configurations of leads 18, 20, and 28 and electrodes carried by leads 18, 20, and 28 are merely exemplary. Other configurations, e.g., numbers and positions of leads and electrodes are also contemplated. For example, in other implementations, IMD 16 may be coupled to additional leads or lead segments having one or more electrodes positioned at different locations proximate the spinal cord or in the pelvic region of patient 14. The additional leads may be used for delivering different stimulation therapies or other electrical stimulations to respective stimulation sites within patient 14 or for monitoring at least one physiological parameter of patient 14.

In accordance with some examples of the disclosure, IMD 16 delivers electrical stimulation periodically or continuously over an extended period of time, e.g., chronic stimulation, to at least one of a spinal nerve, a sacral nerve, a pudendal nerve, dorsal genital nerve, a tibial nerve, an inferior rectal nerve, or a perineal nerve, to produce a therapeutic effect, such as contraction or relaxation of bladder or sphincter muscles. This chronic stimulation may include bursts of pulses instead of a continuous train of pulses. As further described herein, the burst frequency may vary during stimulation and the intra-burst pulse frequency may be varied during stimulation. The intra-burst pulse frequency variation may be consistent between bursts, or the pulse frequency variation may change between bursts, i.e., such that the intra-burst pulse frequency variation for one burst may be the same as or different than the intra-burst pulse frequency for another burst. In some examples, the therapeutic effect may be an inhibitory physiological response related to voiding of patient 14, such as a reduction in bladder contraction frequency or anal sphincter contraction frequency, or relaxation of urethral or anal sphincter pressure. In other examples, the therapeutic effect may be a physiological response that promotes bladder muscle contraction, or in some cases increases urethral sphincter pressure or anal sphincter pressure.

A stimulation program may define various parameters of the stimulation pulses and electrode configuration which result in the electrical stimulation. In some examples, the stimulation program defines parameters for at least one of a current or voltage amplitude of the stimulation signal, a frequency or pulse rate of the stimulation pulses, the shape of the stimulation waveform, a duty cycle of the stimulation, a pulse width of the stimulation pulses, the burst frequency, an intra-burst pulse frequency variation, and/or the combination of electrodes 29 and respective polarities of the subset of electrodes 29 used to deliver the stimulation.

Delivery of electrical stimulation as described in this disclosure may be configured to reduce neuron habituation or other forms of patient adaptation to the stimulation therapy and extend an effective lifetime of the stimulation therapy (e.g., the time for which the stimulation therapy is efficacious in reducing bladder contraction frequency). It has been found that a patient may adapt to stimulation delivered by an IMD over time, such that a certain level of electrical stimulation provided to a tissue site in a patient may be less effective over time, particularly when delivered on a continuous basis. This phenomenon may be referred to as "adaptation." As a result, beneficial effects of electrical stimulation may decrease over time for a patient. Although the electrical stimulation levels (e.g., amplitude of the electrical stimulation signal) may be increased to overcome such adaptation, the increase in stimulation levels may consume more power, and may eventually reach undesirable levels of stimulation, causing discomfort and/or a greater degree or acceleration of adaptation. Electrical stimulation using bursts of pulses may still provide therapeutic effects to patient 14 without continuously delivering pulses. Delivering bursts of pulses, in addition to varying the frequency of pulses within the bursts, may reduce the adaptation of patient 14 to the stimulation.

Determination of the electrical stimulation parameters, including the intra-burst pulse frequency variation, may be performed by a user (e.g., a clinician or patient 14). For example, the clinician may use past experiences with other patients when selecting stimulation parameters appropriate for stimulation therapy. Alternatively, or in addition, the clinician may experimentally determine effective stimulation parameters in the clinic and/or as patient 14 evaluates different parameters during use. For example, the clinician may try several different stimulation parameter sets, e.g., programs, to identify those parameters that sufficiently alleviate the symptoms of patient 14. The clinician may evaluate different intra-burst pulse frequency variations, for example, or provide programs to patient 14 that include different intra-burst pulse frequency variations. These different intra-burst pulse frequency variations may have different profiles (e.g., linear, exponential, polynomial, or random profiles) and/or different rates of variation within each profile. In this manner, patient 14 may discover an effective intra-burst pulse frequency variation, and other parameters, to treat an identified disorder.

In other examples, determining the most effective intra-burst pulse frequency variation may require less of a trial-and-error approach. From the muscle or nerve that will eventually receive the electrical stimulation, IMD 16 may detect intrinsic nerve impulse frequency variation, e.g., using sense electrodes. For example, IMD 16 may use one or more of electrodes 29 to sense the nerve impulses and an impulse sensing module to characterize the impulses, e.g., in terms of burst frequency, intra-burst pulse frequency, and intra-burst pulse frequency variation. IMD 16 may be configured to determine the frequency and/or amplitude of the impulses, e.g., using digital signal processing or other techniques. The clinician may use this nerve impulse frequency variation information to select appropriate burst frequencies, intra-burst pulse frequencies, and intra-burst pulse frequency variations, including pulse frequency variation profiles and rates of frequency change. In one example, the clinician may determine a frequency variation profile for a burst of stimulation pulses that mimics the impulse frequency variation in an intrinsic burst of nerve impulses sensed from the individual patient or, alternatively, determined from some patient population.

In another example, the clinician may determine an inverse intra-burst pulse frequency variation profile that varies the frequency of pulses in a way that is approximately inverse to the variation of an intrinsic burst of impulses. For example, if pulses in an intrinsic burst vary from higher pulse frequency to lower pulse frequency over the course of a burst, an burst of electrical stimulation pulses delivered by the IMD may be configured to vary in an approximately inverse manner, from a lower pulse frequency to a higher pulse frequency over the course of the burst, or vice versa. An inverse pulse variation profile may be effective to disrupt, neutralize, counteract or inhibit the intrinsic nerve impulses, among other uses. Although the clinician may still evaluate different stimulation parameters, detecting intrinsic nerve impulse frequency variation may reduce the amount of time needed to identify effective stimulation parameters.

In some examples, IMD 16 may deliver the stimulation therapy in an open loop manner, in which stimulation with intra-burst pulse frequency variation continues as requested by patient 14 or scheduled based on one or more timers. For example, patient 14 may use programmer 24 to request the initiation of stimulation delivery and/or request the termination of the stimulation. In other examples, the stimulation delivery may be scheduled for certain times of day, operate according to an "ON" and "OFF" duty cycle, or occur on a continuous basis. Of course, during the course of therapy, patient 14 or the clinician may adjust one or more stimulation parameters or select one or more different therapy programs that change the electrical stimulation delivered to patient 14.

In other implementations, IMD 16 may deliver the electrical stimulation in a closed loop manner. For example, IMD 16 may sense an increased pressure of bladder 12 with sensor 22 and initiate electrical stimulation to reduce the possibility of incontinence. In another example, IMD 16 may deliver stimulation based on detected contractions of bladder 12. IMD 16 may establish a baseline contraction frequency of bladder 12 or the baseline contraction frequency may be stored in a memory of IMD 16 or another device (e.g., programmer 24). IMD 16 may then detect contractions of bladder 12 via one or more sensing devices, such as, for example, electrodes 19 or 21, or sensor 22. IMD 16 may detect contractions of bladder 12 based on, for example, bladder impedance, bladder pressure, pudendal or sacral afferent nerve signals, a urinary sphincter EMG, or any combination thereof. IMD 16 then may utilize the sensed contractions of bladder 12 to determine a baseline contraction frequency of bladder 12, e.g., as a number of contractions of bladder 12 per unit time. The baseline contraction frequency of bladder 12 may represent the patient state when no therapeutic effects from delivery of stimulation by IMD 16 are present. In some cases, however, patient 14 may also receive other types of therapy for managing bladder dysfunction, such as a pharmaceutical agent. The baseline contraction frequency of bladder 12 may represent the patient state when patient 14 is under the influence of the pharmaceutical agent.

After determining a baseline contraction frequency, IMD 16 may then sense via electrodes 19 or 21 or sensor 22 a contraction frequency of bladder 12. When the contraction frequency rises above the baseline contraction frequency, for example, IMD 16 may deliver the electrical stimulation. Reducing the bladder contraction frequency may reduce the possibility of an incontinence event. After the contraction frequency falls below the baseline contraction frequency, or some other therapeutic threshold, IMD 16 may cease delivering the electrical stimulation. IMD 16 may again deliver stimulation upon a subsequent increase in bladder contraction frequency. IMD 16 may also, or alternatively, use other physiological states to determine when to deliver the stimulation therapy.

In another example, IMD 16 may sense bladder fullness in a close loop manner to provide electrical stimulation to alleviate urinary retention. For example, IMD 16 may sense an increased pressure of bladder 12 with sensor 22 and initiate electrical stimulation to promote bladder voiding. In another example, IMD 16 may deliver stimulation based on detected contractions of bladder 12. IMD 16 may detect contractions of bladder 12 or bladder fill level based on, for example, bladder impedance, bladder pressure, pudendal or sacral afferent nerve signals, a urinary sphincter EMG, or any combination thereof. IMD 16 then may utilize the sensed contractions or fill level, as applicable, to determine when to deliver electrical stimulation. When the contractions or fill level are below a desired threshold, IMD 16 may terminate stimulation and then restart stimulation later when the applicable threshold is exceeded, thereby providing closed loop stimulation when needed. In the example of bladder contraction frequency, the delivery of electrical stimulation with an intra-burst pulse frequency variation inverted from intrinsic impulse frequencies may act to disrupt bladder contractions. In other words, stimulation with inverted intra-burst pulse frequency variations may reduce the frequency of bladder contractions. In other examples, stimulation with inverted intra-burst pulse frequency variations may act to interfere with pain impulses to treat pelvic pain.

In the example shown in FIG. 1, IMD 16 may determine impedance of bladder 12 using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine impedance of bladder 12 based on the transmitted electrical signal. Such an impedance measurement may be utilized to determine response of contractions of bladder 12 during electrical stimulation and/or to determine a fullness of bladder 12, or the like. Although fullness may be a physiological state indicative of the need for therapy, fullness may also indicate that the frequency of bladder contractions will increase to void bladder 12.

In the example four-wire arrangement shown in FIG. 1, electrodes 19A and 21A and electrodes 19B and 21B, may be located substantially opposite each other relative to the center of bladder 12. For example electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 19 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced the determined voltage.

In other examples, electrodes 19 and 21 may be used to detect an EMG of the detrusor muscle. This EMG may be used to identify the frequency of bladder contractions and the physiological state of patient 12. The EMG may also be used to detect the strength of the bladder contractions in some examples. Alternatively, or in addition, to an EMG, a strain gauge or other device may be used to detect the status of bladder 12.

In the example of FIG. 1, IMD 16 also includes a sensor 22 for detecting changes to bladder 12. Sensor 22 may include, for example, a pressure sensor for detecting changes in bladder pressure, electrodes for sensing pudendal or sacral afferent nerve signals, electrodes for sensing urinary sphincter EMG signals (or anal sphincter EMG signals in examples in which system 10 provides therapy to manage fecal urgency or fecal incontinence), or any combination thereof. In examples in which sensor 22 is a pressure sensor, the pressure sensor may be a remote sensor that wirelessly transmits signals to IMD 16 or may be carried on one of leads 18, 20, or 28 or an additional lead coupled to IMD 16. In some examples, IMD 16 may determine whether a contraction frequency of bladder 12 has occurred based on a pressure signal generated by sensor 22. In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMG, the sense electrodes may be carried on one of leads 18, 20, or 28 or additional leads coupled to IMD 16. In any case, in some examples, IMD 16 may control the timing of the delivery of the electrical stimulation with the intra-burst pulse frequency variation based on input received from sensor 22.

In other examples, sensor 22 may comprise a patient motion sensor in IMD 16 that generates a signal indicative of patient activity level or posture state. IMD 16 may deliver electrical stimulation to control urge incontinence that results from certain posture states of activities of patient 14. For example, sensor 22 may detect that patient 14 is riding in a car. In response, IMD 16 may begin stimulation therapy to help patient 14 avoid an incontinence event. In this manner, IMD 16 may be responsive to external patient activities instead of merely internal organ functions.

System 10 may also include an external programmer 24, as shown in FIG. 1. Programmer 24 may be a clinician programmer or patient programmer. In some examples, programmer 24 may be a wearable communication device, with a therapy request input integrated into a key fob or a wrist watch, handheld computing device, computer workstation, or networked computing device. Programmer 24 may include a user interface that receives input from a user (e.g., patient 14, a patient caretaker or a clinician). In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 and/or ICD 16 remotely via a networked computing device.

A user, such as a physician, technician, surgeon, electrophysiologist, or other clinician, may also interact with programmer 24 or another separate programmer (not shown), such as a clinician programmer, to communicate with IMD 16. Such a user may interact with a programmer to retrieve physiological or diagnostic information from IMD 16. The user may also interact with a programmer to program IMD 16, e.g., select values for the stimulation parameter values with which IMD 16 generates and delivers stimulation and/or the other operational parameters of IMD 16, such as the intra-burst pulse frequency variation. Programmer 24 may also be used to generate multiple different programs selectable by patient 14 that include different profiles of the intra-burst pulse frequency variation. In this manner, patient 14 may evaluate the efficacy from stimulation therapy defined by different intra-burst pulse frequency variations.

In one example, the user may use programmer 24 to retrieve information from IMD 16 regarding the contraction frequency of bladder 12 and/or voiding events. As another example, the user may use a programmer to retrieve information from IMD 16 regarding the performance or integrity of IMD 16 or other components of system 10, such as leads 18, 20, and 28, or a power source of IMD 16. In some examples, this information may be presented to the user as an alert if a system condition that may affect the efficacy of therapy is detected.

In some examples in, patient 14 may interact with programmer 24 to control IMD 16 to deliver the electrical stimulation, e.g., to begin the stimulation therapy upon urge incontinency. Patient 14 may, for example, use a keypad or touch screen of programmer 24 to cause IMD 16 to deliver or stop the electrical stimulation, such as when patient 14 senses that a leaking episode may be imminent. In this way, patient 14 may use programmer 24 to provide a therapy request to deliver electrical stimulation "on demand," e.g., when patient 14 deems the stimulation therapy desirable.

In some examples, programmer 24 may provide a notification to patient 14 when the electrical stimulation is being delivered or notify patient 14 that stimulation therapy may be effective. In such examples, programmer 24 may display a visible message, emit an audible alert signal or provide a somatosensory alert (e.g., by causing a housing of programmer 24 to vibrate).

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
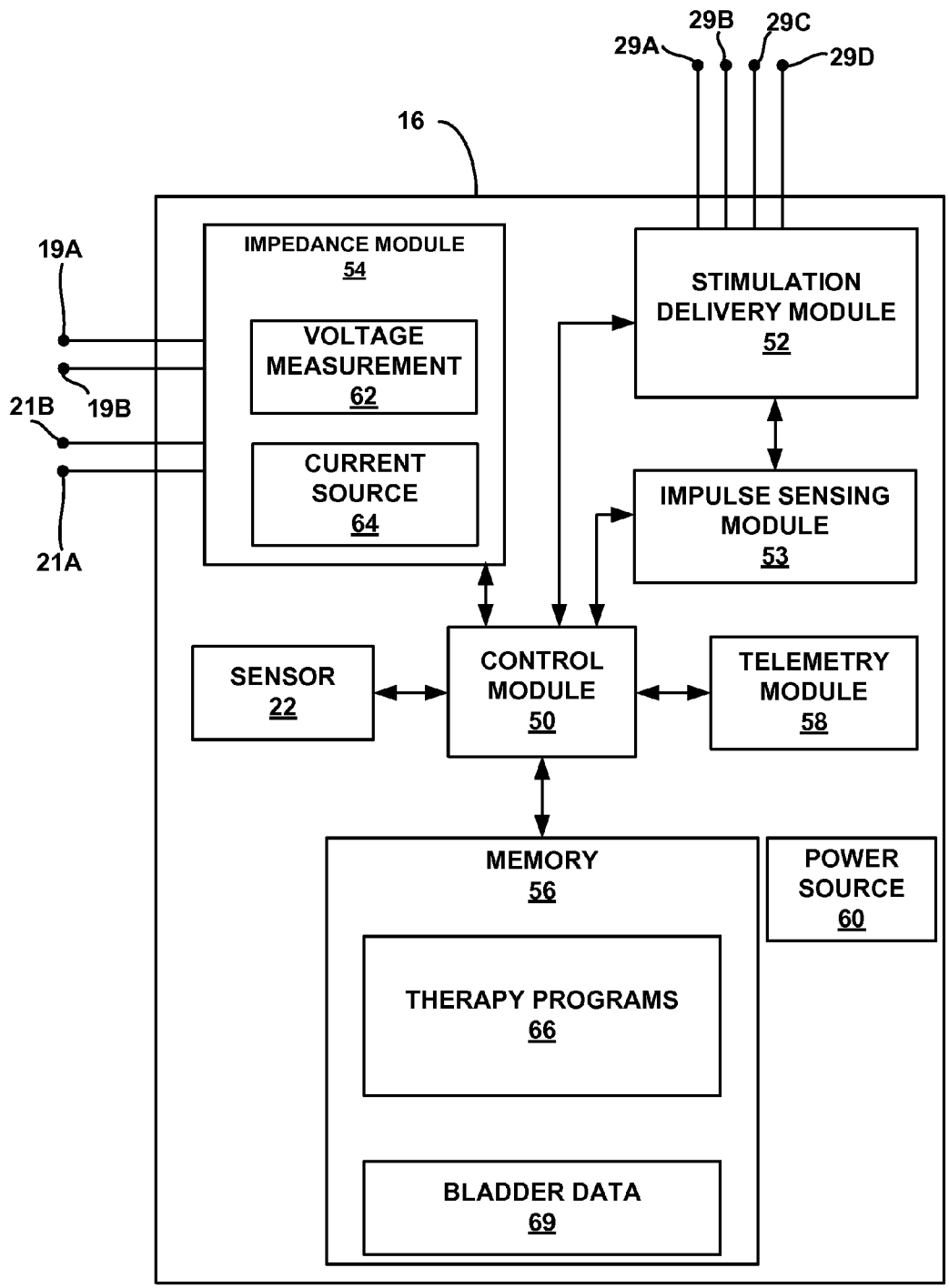
FIG. 2 is a block diagram illustrating an example configuration of an implantable medical device (IMD) which may be utilized in either of the systems of FIG. 1 or 2.

FIG. 2 is a block diagram illustrating example components of IMD 16. In the example of FIG. 2, IMD 16 includes sensor 22, control module 50, stimulation delivery module 52, impulse sensing module 53, impedance module 54, memory 56, telemetry module 58, and power source 60. Each of these components, such as control module 50 and stimulation delivery module 52, may be housed within IMD 16. In other examples, IMD 16 may include more or fewer components. For example, in some examples, such as examples in which IMD 16 deliver the electrical stimulation in an open-loop manner, IMD 16 may not include sensor 22 and/or impedance module 54.

In general, IMD 16 may comprise any suitable arrangement of hardware, alone or in combination with software and/or firmware, to perform the techniques attributed to IMD 16 and control module 50, stimulation delivery module 52, impulse sensing module 53, impedance module 54, and telemetry, module 58 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. For example, control module 50 may include one or more processors. IMD 16 also, in various examples, may include a memory 56, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although control module 50, stimulation delivery module 52, impulse sensing module 53, impedance module 54, and telemetry module 58 are described as separate modules, in some examples, control module 50, stimulation delivery module 52, impulse sensing module 53, impedance module 54, and telemetry module 58 are functionally integrated. In some examples, control module 50, stimulation delivery module 52, impulse sensing module 53, impedance module 54, and telemetry module 58 correspond to individual hardware units, such as ASICs, DSPs, FPGAs, or other hardware units.

Memory 56 stores therapy programs 66 that specify stimulation parameter values for the sub-threshold electrical stimulation provided by IMD 16. In some examples, memory 56 also stores bladder data 69, which control module 50 may use for controlling the timing of the delivery of the sub-threshold electrical stimulation (e.g., beginning and termination of the sub-threshold electrical stimulation). For example, bladder data 69 may include threshold values or baseline values for at least one of bladder impedance, bladder pressure, bladder fill level, sacral or pudendal afferent nerve signals, bladder contraction frequency, or external urinary sphincter EMG templates. As described in further detail below, the threshold values and baseline values may indicate a particular physiological state, such as a bladder contraction (e.g., for bladder urgency), bladder fill level (e.g., for urine retention or incontinence) or a condition indicative of a voiding-related physiological condition (e.g., a patient state in which there is a relatively high likelihood of an involuntary voiding event) usable as a therapy trigger event.

Memory 56 may also store instructions for execution by control module 50, in addition to therapy programs 66 and bladder data 69. Therapy programs 66 may include one or more programs that define a set of stimulation parameters (e.g., amplitude, pulse width, burst frequency, or intra-burst pulse frequency variation). Therefore, each of therapy programs 66 may vary by a single parameter or multiple parameters. In some examples, therapy programs 66 may define groups of therapy programs, where each program group is directed at a particular therapy. Information related to sensed bladder contractions, bladder fill level, bladder impedance and/or posture of patient 14 may be recorded for long-term storage and retrieval by a user, and/or used by control module 50 for adjustment of stimulation parameters (e.g., amplitude, pulse width, burst frequency, or intra-burst pulse frequency variation). In some examples, memory 56 includes separate memories for storing instructions, electrical signal information, therapy programs 66, and bladder data 69.

Generally, stimulation delivery module 52 generates and delivers electrical stimulation therapy under the control of control module 50. In some examples, control module 50 controls stimulation delivery module 52 by accessing memory 56 to selectively access and load at least one of therapy programs 66 to stimulation delivery module 52. For example, in operation, control module 50 may access memory 56 to load one of therapy programs 66 to stimulation delivery module 52.

By way of example, control module 50 may access memory 56 to load one of therapy programs 66 to stimulation delivery module 52 for delivering the electrical stimulation therapy to patient 14. A clinician or patient 14 may select a particular one of therapy programs 66 from a list using a programming device, such as programmer 24 or a clinician programmer. Control module 50 may receive the selection via telemetry module 58. Stimulation delivery module 52 delivers the electrical stimulation to patient 14 according to the selected program for an extended period of time, such as minutes, hours, days, weeks, or until patient 14 or a clinician manually stops or changes the program. During the time of delivery with the program, the electrical stimulation may not be delivered the entire time. Instead, delivery with a program generally indicates that the program may control when stimulation is delivered to patient 14. In other examples, control module 50 may determine the timing with which IMD 16 delivers stimulation to patient 14 according to different programs based on sensor input or patient input.

Stimulation delivery module 52 delivers electrical stimulation according to stimulation parameters. In some examples, stimulation delivery module 52 delivers electrical stimulation therapy in the form of electrical pulses. In such examples, relevant stimulation parameters may include a voltage amplitude, a current amplitude, an intra-burst pulse frequency variation (e.g., as indicated by a profile), a pulse width, a burst frequency, a duty cycle, a burst duty cycle, or the combination of electrodes 29 that stimulation delivery module 52 uses to deliver the stimulation signal. In other examples, stimulation delivery module 52 delivers electrical stimulation in the form of continuous waveforms. In such examples, relevant stimulation parameters may include a voltage amplitude, a current amplitude, a frequency, a shape of the stimulation signal, a duty cycle of the stimulation signal, or the combination of electrodes 29 stimulation delivery module 52 uses to deliver the stimulation signal. Although an intra-burst pulse frequency variation is generally applicable to electrical pulses, continuous waveforms may be similarly delivered in bursts and varied in frequency within each burst.

In some examples, the stimulation parameters for the therapy programs 66 may be selected to relax bladder 12, e.g., to reduce a frequency of contractions of bladder 12, to promote bladder contraction, or to increase or decrease sphincter pressure. An example range of stimulation parameters for the electrical stimulation that are likely to be effective in treating bladder dysfunction, e.g., upon application to the spinal, sacral, pudendal, tibial, dorsal genital, inferior rectal, or perineal nerves, are as follows:

1. Intra-burst pulse frequency or pulse rate: between about 0.1 Hz and about 5000 Hz, such as between about 1 Hz and about 100 Hz, between about 20 Hz and about 40 Hz, or about 30 Hz.

2. Pulse amplitude: between about 0.1 volts and about 50 volts, such as between about 0.5 volts and about 20 volts, or between about 1 volt and about 10 volts. Alternatively, the pulse amplitude may be between about 0.1 milliamps (mA) and about 50 mA, such as between about 0.5 mA and about 20 mA, or between about 1 mA and about 10 mA.

3. Pulse width: between about 10 microseconds (μs) and about 5000 μs, such as between about 100 μs and about 1000 μs, or between about 100 μs and about 250 μs.

4. Inter-burst interval: between about 1 milliseconds (ms) and about 5000 ms, such as between about 10 ms and about 1000 ms, or between about 30 ms and about 200 ms.

5. Number of pulses per burst: between about 2 and 1000 pulses, such as between about 2 and about 100 pulses, or between about 3 and about 30 pulses.

Although voltage amplitudes are provided above, alternatively, pulses may be controlled according to current amplitudes. In addition to these general pulse parameters, therapy programs 66 may define additional parameter values for a burst frequency (e.g., inter-burst frequency) and an intra-burst pulse frequency variation. The burst frequency may generally be between approximately 1 Hz and 100 Hz. More specifically, the burst frequency may be between approximately 20 Hz and 40 Hz. Although the inter-burst frequency may generally be consistent over time, a therapy program may provide for inter-burst frequency variation over time. This inter-burst frequency variation may be selected to compensate for nerve adaptation or capture different muscle fibers, for example. In some examples, the inter-burst frequency variation may have a linear, exponential, polynomial, or random profile over time.

As one example, the range of pulse frequencies for the intra-burst pulse frequency variation is selected to affect nerves innervating the pelvic floor. These affected nerves may be involved in the control of urinary or fecal retention and urgency and frequency disorders. Therefore, an intra-pulse frequency variation between approximately 20 and 40 Hz, for example, is selected to target these specific nerve fibers and treat these disorders of the pelvic floor. As further described herein, the detected intrinsic nerve impulse frequency range for these targeted nerves may be between approximately 20 and 40 Hz. Although the intra-burst frequencies may not be selected only to reflect the frequency variations of intrinsic nerve impulses, the nerve impulse parameters may be a basis for stimulation parameters.

Recorded afferent nerve signals have been observed, for certain nerves, to have a burst frequency in a range of 50-67 Hz or 20-40 Hz, an inter-burst interval of 50-200 milliseconds or 33-75 milliseconds, and a number of pulses per burst of 3-22 pulses or 3-18 pulses. In some examples, bursts of stimulation pulses may be delivered with parameters corresponding or similar to the burst frequency, inter-burst interval and number of pulses mentioned immediately above, e.g., if it is desired to mimic such afferent nerve signals.

Therapy programs 66 may also define a variation in pulse frequency within bursts of pulses. Generally, this intra-burst pulse frequency may vary between 5 Hz and 250 Hz, or more specifically, between approximately 20 Hz and 40 Hz. The intra-burst pulse frequency may vary within a predetermined range of frequencies, e.g., approximately 20 Hz to 40 Hz. However, in other examples, only a subset of the pulse frequencies may fall within the range. For example, the pulse frequency may begin within the range and end outside of the range, or vice versa, over the course of a burst.

In some examples, the intra-burst pulse frequency variation may stay the same between each burst. In other words, the pulses within each burst are substantially identical. In other examples, the intra-burst pulse frequency variation may change from one burst to the next or change at one or more times during therapy. This inter-burst pulse frequency variation may allow the stimulation to capture different muscle or nerve fibers, reduce adaptation, or allow the therapy to adapt to changing physiological circumstances. For example, as described in further detail below, the inter-burst pulse frequency variation may allow the stimulation to adjust to changing intrinsic nerve impulses.

The intra-burst pulse frequency may be varied in a variety of ways. For example, the pulse frequency within each burst may either increase over time or decrease over time. In other examples, the pulse frequency may increase and decrease, in any combination, within a single burst. In other examples, the pulse frequency may be randomly varied within each burst of pulses. Random variation may be useful to capture different nerve or muscle fibers, or prevent adaptation, for example.

In addition, the intra-burst pulse frequency may be varied according to a variation profile that characterizes how the frequency is varied over time. For example, a linear profile may indicate that the intra-burst pulse frequency is linearly varied over time. In another example, an exponential profile may indicate that the intra-burst pulse frequency is exponentially varied over time. In other words, the pulse frequency may increasingly increase or decreased within each burst. In a further example, a polynomial profile may indicate that the intra-burst pulse frequency is varied over time according to a polynomial equation. In this manner, the clinician or control module 50 may create a curve fit that defines two or more changes in frequency variation within a single burst. An example of a polynomial profile is provided in FIG. 5B. In some examples, the variation profile may be selected such that the pulses in a burst generally or approximately mimic the variation of pulses in an intrinsic burst of nerve impulses in the patient. The variation profile may be selected, for example, by reference to sensed nerved impulses of an individual patient or patient population, or based on expected variation of such nerve impulses, or based on other criteria or methods.

In some examples, in addition to frequency variation, a therapy program may vary at least one of a current amplitude or a voltage amplitude of pulses within a burst of pulses. This amplitude variation may occur substantially similarly to the intra-burst pulse frequency variation described above, but amplitude is varied instead of frequency. Accordingly, any other parameters may be similarly changed within a burst of pulses. In addition, multiple parameters may be varied within the same burst. For example, a burst may include intra-burst pulse frequency variation and amplitude variation, and variation may be the same or different from burst to burst.

Impulse sensing module 53 may detect one or more parameters of intrinsic nerve impulses via electrodes 29. In this manner, impulse sensing module 53 may detect a frequency variation of intrinsic nerve impulses within a burst of impulses, in addition to impulse amplitude, width, and other parameters. The detected frequency variation of intrinsic nerve impulses may be used by control module 50 to mimic or invert the intrinsic signals by appropriately varying the intra-burst pulse frequency of the delivered stimulation therapy. For example, control module 50 may determine an inverse pulse frequency variation based on the frequency variation of the intrinsic nerve impulses. In this manner, control module 50 may be able to directly target intrinsic impulses to inhibit or disrupt nerve signals for therapy.

As shown in FIG. 2, impulse sensing module 53 may communicate with stimulation delivery module 52 to detect the nerve impulses using one or more of stimulation electrodes 29 or using dedicated sense electrodes. In other examples, impulse sensing module 53 may directly couple to electrodes 29 or other electrodes (not shown) to detect the parameters of intrinsic nerve impulses. Although impulse sensing module 53 may detect nerve impulses when stimulation is not delivered, impulse sensing module 53 may be configured to detect nerve impulses during stimulation therapy. In this manner, impulse sensing module 53 may detect the most recent impulses and control module 50 may adjust the intra-burst pulse frequency variation as needed based on the detection. In other words, control module 50 may update the determination of the intra-burst pulse frequency variation.

Control module 50 may also update the determination of the intra-burst pulse frequency variation, e.g., an inverse pulse frequency variation, upon the detection of an update event. This update event may indicate that control module 50 should identify any changes to the nerve impulse frequency. Example update events may include the detection of a predetermined number of bursts of impulses, an expiration of a predetermined time period, an ineffective therapy, or a user request to update the determination of the frequency variation. In other words, control module 50 may use recently detected impulse frequencies to update stimulation therapy after certain update events that may indicate when previous detected impulse frequencies may no longer be accurate. This update event may be time-based or therapy-based. For example, if the detection of bladder contractions during stimulation indicates that the therapy is not effective, the control module 50 may attempt to adjust stimulation according to any intrinsic impulse changes.

In some examples, at least one of therapy programs 66 defines stimulation parameters that cause stimulation delivery module 52 to deliver electrical stimulation to patient 14 in a closed loop manner. In closed loop stimulation therapy, control module 50 or stimulation delivery module 52 may deliver stimulation therapy to patient based on at least one feedback, e.g., a signal representative of a detected physiological state of patient 14 sensed by at least one of sensor 22, electrode 19, or electrode 21. Control module 50 may start or stop the delivery therapy, or deliver therapy with a different therapy program, based on the detected physiological state. For example, control module 50 or stimulation delivery module 52 may control delivery of electrical stimulation by stimulation delivery module 52 based on a contraction frequency of bladder 12.

To facilitate delivery of stimulation in a closed loop manner, the at least one of therapy programs 66 may include a baseline contraction frequency or a threshold contraction frequency. The baseline contraction frequency may be contraction frequency of bladder 12 at a time prior to delivery of the electrical stimulation by stimulation delivery module 52. For example, the baseline contraction frequency of bladder 12 may be sensed and determined by control module 50 after implantation of IMD 16 in patient 14, but before stimulation delivery module 52 delivers electrical stimulation to patient 14. In some examples, the baseline contraction frequency of bladder 12 may represent the patient state when no therapeutic effects from delivery of stimulation by IMD 16 are present.

Control module 50 may determine the baseline contraction frequency of bladder 12 utilizing signals representative of physiological parameters received from at least one of sensor 22, electrodes 19 or electrodes 21. In some examples, control module 50 monitors impedance of bladder 12 to detect contraction of bladder 12 based on signals received from impedance module 54. For example, control module 50 may determine an impedance value based on signals received from impedance module 54 and compare the determined impedance value to a threshold impedance value stored in memory 56 as bladder data 69. When the determined impedance value is less than the threshold value stored in bladder data 69, control module 50 detects bladder contraction. In some implementations, control module 50 monitors impedance of bladder 12 for a predetermined duration of time to detect contractions of bladder 12, and determines the baseline contraction frequency of bladder 12 by determining a number of contractions of bladder 12 in the predetermined duration of time. In other examples, electrodes 19 or 21 may be used to detect an EMG of the detrusor muscle to identify bladder contraction frequencies. Alternatively, a strain gauge or other measure of bladder contraction change may be used to detect the physiological state of bladder 12. As mentioned above, alternatively or additionally; other conditions such as a bladder fill level may be determined, e.g., in relation to delivery of stimulation by IMD 16 for bladder urgency, urine retention or other dysfunction or disorders.

In an example closed loop design, for the example of bladder urgency; control module 50 may begin the electrical stimulation upon the detection of an increasing bladder contraction frequency indicative of urge incontinence. This physiological state of bladder 12 may indicate that stimulation may alleviate the increase in bladder contractions. In other examples of closed loop stimulation, control module 50 may control the delivery of intra burst pulse frequency variation therapy based on other physiological states, e.g., bladder pressure, posture state, or patient activity level.

In the example illustrated in FIG. 2, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, control module 50 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy to bladder 12, e.g., sub-threshold signals, due to, for example, the amplitudes or widths of such signals and/or the timing of delivery of such signals. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Control module 50 determines an impedance value from the measure voltage values received from voltage measurement circuitry 52.

In other examples, control module 50 may monitor signals received from sensor 22 to detect contraction of bladder 12 and determine the baseline contraction frequency. In some examples, sensor 22 may be a pressure sensor for detecting changes in pressure of bladder 12, which control module 50 may correlate to contractions of bladder 12. Control module 50 may determine a pressure value based on signals received from sensor 22 and compare the determined pressure value to a threshold value stored in bladder data 69 to determine whether the signal is indicative of a contraction of bladder 12. In some implementations, control module 50 monitors pressure of bladder 12 to detect contractions of bladder 12 for a predetermined duration of time, and determines a contraction frequency of bladder 12 by calculating a number of contractions of bladder 12 in the predetermined time period.

In other examples, control module 50 may cause a threshold contraction frequency to be stored as bladder data 69 in memory 56, and may utilize the threshold contraction frequency to deliver electrical stimulation in a closed loop manner. In some implementations, control module 50 may, automatically or under control of a user, determine the threshold contraction frequency based on a baseline contraction frequency. For example, control module 50 may determine the threshold contraction frequency as a predetermined percentage of the baseline contraction frequency or a percentage of the baseline contraction frequency input by a user via programmer 24. As one example, the threshold frequency may be between approximately 75% and approximately 100% of the baseline contraction frequency.

In some examples, the threshold contraction frequency may not be based on a baseline contraction frequency of patient 12, and may instead be based on clinical data collected from a plurality of patients. For example, the threshold contraction frequency may be determined based on an average bladder contraction frequency of a plurality of patients during a bladder filling time period, i.e., during a time period in which the plurality of patients are not experiencing a voluntary or involuntary voiding event. In any case, the threshold contraction frequency may be stored in bladder data 69, and, in some examples, control module 50 may utilize the threshold contraction frequency as a comparison to detected bladder contractions when delivering stimulation therapy in a closed loop manner to patient 14.

In other examples, instead of utilizing a threshold contraction frequency or a baseline contraction frequency from other patients, control module 50 may control closed-loop delivery of stimulation therapy based on EMG signals. In some implementations, sensor 22 may include an EMG sensor, and control module 50 may generate an EMG from the received signals generated by sensor 22. Sensor 22 may be implanted proximate to a muscle which is active when bladder 12 is contracting, such as a detrusor muscle. Control module 50 may compare an EMG collected during the second time period to EMG templates stored as bladder data 69 (e.g., a short-term running average) to determine whether the frequency of bladder contractions indicate a return to a baseline contraction frequency or deviation from the baseline. In some cases, control module 50 may generate the EMG template based on received signals generated by sensor 22 after implantation of IMD 16, but before stimulation delivery module 52 delivers any stimulation therapy to patient 14.

Control module 52, then, may utilize at least one of a threshold contraction frequency, a baseline contraction frequency, fill level, detected EMG signals or other sensed parameters to control stimulation delivery module 52 to deliver stimulation therapy in a closed loop manner. For example, during at least the second time periods, control module 50 may monitor impedance of bladder 12 to detect contraction of bladder 12 based on signals received from impedance module 54. In some implementations, control module 50 substantially continuously monitors impedance of bladder 12, at least during the second time periods, to detect contraction of bladder 12, and determines a contraction frequency of bladder 12 by determining a number of contractions of bladder 12 in a specified time period.

In other examples, sensor 22 may be a pressure sensor and control module 50 may monitor signals received from sensor 22 during at least a portion of the second time period to detect contraction of bladder 12. In some implementations, control module 50 substantially continuously monitors pressure of bladder 12, at least during the second time periods, to detect contraction of bladder 12, and determines a contraction frequency of bladder 12 by determining a number of contractions of bladder 12 in a specified time period.

After determining a contraction frequency of bladder 12, control module 50 may compare the determined contraction frequency of bladder 12 to the threshold contraction frequency stored in memory 56 as bladder data 69. When the determined contraction frequency is greater than or substantially equal to the threshold contraction frequency stored in bladder data 69, control module 50 may control stimulation delivery module 52 to initiate delivery of electrical stimulation to patient 14.

In other examples, control module 50 may compare the determined contraction frequency of bladder 12 and the baseline contraction frequency to determine a difference between the determined contraction frequency and the baseline contraction frequency. In some examples, when the difference is less than or equal to a specified value (e.g., a threshold difference value) control module 50 may cause stimulation delivery module 52 to initiate delivery of electrical stimulation to patient 14.

In other examples, sensor 22 may include an EMG sensor, and processor 50 may generate an EMG from the received signals generated by sensor 22 (e.g., which may sense the muscle activity with one or more sensor positioned near the target muscle) and compare the EMG to an EMG template stored as bladder data 69 to determine whether the contractions of bladder 12 are indicative of a predetermined characteristic which causes control module 50 to control stimulation delivery module 52 to initiate delivery of the electrical stimulation. For example, the predetermined characteristic may be a frequency of contractions of bladder, an amplitude of the signal (representative of intensity of contractions of bladder 12), or the like.

In the example of FIG. 2, stimulation delivery module 52 drives electrodes on a single lead 28. Specifically, stimulation delivery module 52 delivers stimulation therapy to tissue of patient 14 via selected electrodes 29A-29D carried by lead 28. A proximal end of lead 28 extends from the housing of IMD 16 and a distal end of lead 28 extends to a target therapy site, such as a spinal nerve (e.g., an S3 nerve), or a therapy site within the pelvic floor, such as tissue sites proximate a sacral nerve, a pudendal nerve, a tibial nerve, a dorsal genital nerve, an inferior rectal nerve, a perineal nerve, a hypogastric nerve, a urinary sphincter, or any combination thereof. In other examples, stimulation delivery module 52 may deliver electrical stimulation with electrodes on more than one lead and each of the leads may carry one or more electrodes. The leads may be configured as axial leads with ring electrodes and/or paddle leads with electrode pads arranged in a two-dimensional array. The electrodes may operate in a bipolar or multipolar configuration with other electrodes, or may operate in a unipolar configuration referenced to an electrode carried by the device housing or "can" of IMD 16.

As previously described, in some examples, sensor 22 may comprise a pressure sensor for detecting changes in bladder pressure, electrodes for sensing pudendal or sacral afferent nerve signals, or electrodes for sensing external urinary sphincter EMG signals (or anal sphincter signals in examples in which IMD 16 provides fecal urgency or fecal incontinence therapy, or any combination thereof. Additionally or alternatively, sensor 22 may comprise a motion sensor, such as a two-axis accelerometer, three-axis accelerometer, one or more gyroscopes, pressure transducers, piezoelectric crystals, or other sensors that generate a signal that changes as patient activity level or posture state changes. Control module 50 may detect a patient condition indicative of a high probability of an incontinence event (e.g., bladder contraction or abnormal detrusor muscle activity), or a high bladder fill level, or other trigger events based on signals received from sensor 22 in addition to instead of impedance module 54. Sensor 22 may also be a motion sensor that is responsive to tapping (e.g., by patient 14) on skin superior to IMD 16 and, as previously described, control module 50 may control therapy module 52 to deliver the electrical stimulation in response to detection of the patient tapping.

In examples in which sensor 22 includes a motion sensor, control module 50 may determine a patient activity level or posture state based on a signal generated by sensor 22. This patient activity level may be sitting, exercising, working, running, walking, or any other activity of patient 12. For example, control module 50 may determine a patient activity level by sampling the signal from sensor 22 and determining a number of activity counts during a sample period, where a plurality of activity levels are associated with respective activity counts. In one example, control module 50 compares the signal generated by sensor 22 to one or more amplitude thresholds stored within memory 56, and identifies each threshold crossing as an activity count.

In some examples, control module 50 may control stimulation delivery module 52 to deliver electrical stimulation based on patient input received via telemetry module 58. Telemetry module 58 includes any suitable hardware, firmware, software or any combination thereof for communicating with another device, such as programmer 24 (FIG. 1). Under the control of control module 50, telemetry module 58 may receive downlink telemetry, e.g., patient input, from and send uplink telemetry, e.g., an alert, to programmer 24 with the aid of an antenna, which may be internal and/or external. Control module 50 may provide the data to be uplinked to programmer 24 and the control signals for the telemetry circuit within telemetry module 58, and receive data from telemetry module 58.

Generally, control module 50 controls telemetry module 58 to exchange information with medical device programmer 24 and/or another device external to IMD 16. Control module 50 may transmit operational information and receive therapy programs or stimulation parameter adjustments via telemetry module 58. Also, in some examples, IMD 16 may communicate with other implanted devices, such as stimulators, control devices, or sensors, via telemetry module 58.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

Figure 3:
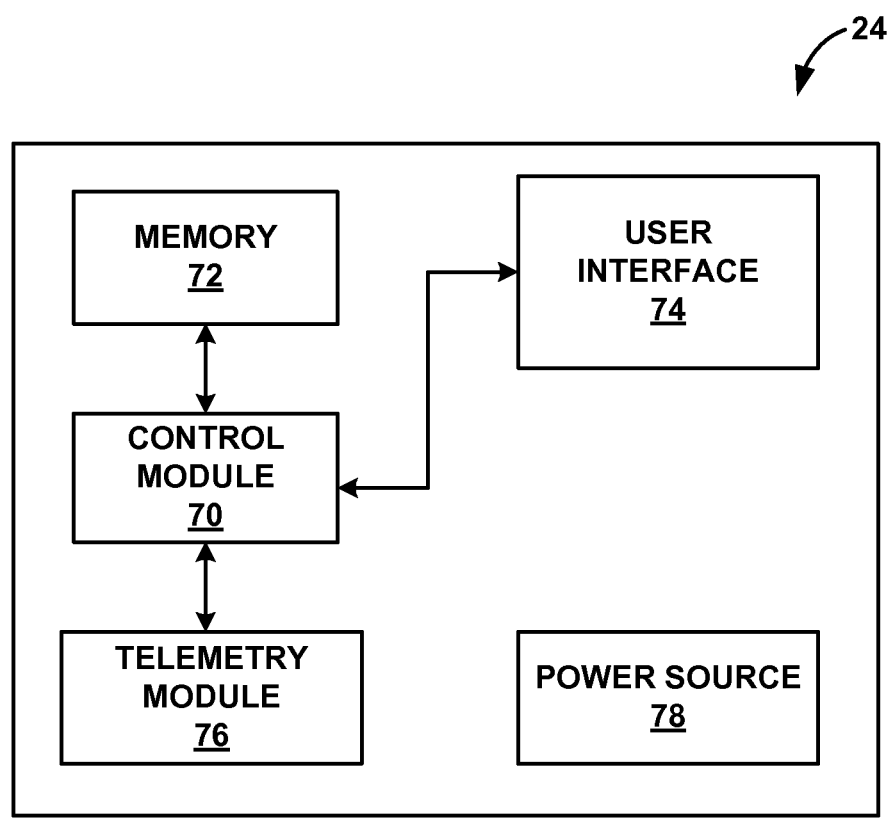
FIG. 3 is a block diagram illustrating an example configuration of an external programmer which may be utilized either of the systems of FIG. 1 or 2.

FIG. 3 is a block diagram illustrating an example configuration of an external programmer 24. While programmer 24 may generally be described as a hand-held computing device, the programmer may be a notebook computer, a cell phone, or a workstation, for example. As illustrated in FIG. 3, external programmer 24 may include a control module 70, memory 72, user interface 74, telemetry module 76, and power source 78. Each of these components, e.g., control module 70 and memory 72, may be housed within programmer 24. Memory 72 may store program instructions that, when executed by control module 70, cause control module 70 and external programmer 24 to provide the functionality ascribed to external programmer 24 throughout this disclosure.

In general, programmer 24 comprises any suitable arrangement of hardware, alone or in combination with software and/or firmware, to perform the techniques attributed to programmer 24, and control module 70, user interface 74, and telemetry module 76 of programmer 24. In various examples, programmer 24 may include one or more processors, such as one or more microprocessors, DSPs, ASICs, FPGAs, or any other equivalent integrated or discrete logic circuitry, as well as any combinations of such components. Programmer 24 also, in various examples, may include a memory 72, such as RAM, ROM, PROM, EPROM, EEPROM, flash memory, a hard disk, a CD-ROM, comprising executable instructions for causing the one or more processors to perform the actions attributed to them. Moreover, although control module 70 and telemetry module 76 are described as separate modules, in some examples, control module 70 and telemetry module 76 are functionally integrated. In some examples, control module 70 and telemetry module 76 and telemetry module 58 correspond to individual hardware units, such as ASICs, DSPs, FPGAs, or other hardware units.

Memory 72 may store program instructions that, when executed by control module 70, cause control module 70 and programmer 24 to provide the functionality ascribed to programmer 24 throughout this disclosure. In some examples, memory 72 may further include program information, i.e., therapy programs defining intra-burst pulse frequency variations of the electrical stimulation, similar to those stored in memory 56 of IMD 16. The therapy programs stored in memory 72 may be downloaded into memory 56 of IMD 16.

User interface 74 may include a button or keypad, lights, a speaker for voice commands, a display, such as a liquid crystal (LCD), light-emitting diode (LED), or cathode ray tube (CRT). In some examples the display may be a touch screen. As discussed in this disclosure, control module 70 may present and receive information relating to electrical stimulation and resulting therapeutic effects via user interface 74. For example, control module 70 may receive patient input via user interface 74. The input may be, for example, in the form of pressing a button on a keypad or selecting an icon from a touch screen.

Control module 70 may also present information to the patient in the form of alerts related to delivery of the electrical stimulation to patient 14 or a caregiver, as will be described in more detail below, via user interface 74. Although not shown, programmer 24 may additionally or alternatively include a data or network interface to another computing device, to facilitate communication with the other device, and presentation of information relating to the sub-threshold electrical stimulation and therapeutic effects after termination of the sub-threshold electrical stimulation via the other device.

Telemetry module 76 supports wireless communication between IMD 16 and programmer 24 under the control of control module 70. Telemetry module 76 may also be configured to communicate with another computing device via wireless communication techniques, or direct communication through a wired connection. Telemetry module 76 may be substantially similar to telemetry module 58 described above, providing wireless communication via an RF or proximal inductive medium. In some examples, telemetry module 76 may include an antenna, which may take on a variety of forms, such as an internal or external antenna. An external antenna that is coupled to programmer 24 may correspond to a programming head that may be placed over IMD 16.

Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

IMD 16 and/or programmer 24 may control of the timing of the delivery of the electrical stimulation to manage bladder dysfunction, for example. If external programmer 24 controls the stimulation, programmer 24 may transmit therapy programs for implementation by control module 50 to IMD 16 via telemetry module 76. A user patient 14 or a clinician) may determine the intra-burst pulse frequency variation for one or more programs. For example, the user may, via user interface 74, define the frequencies of the pulse within each burst and the variation profile for the intra-burst pulse frequencies. In some examples, the user may create one or more programs with different intra-burst pulse frequency variations. In other examples, the user may simply adjust the intra-burst pulse frequency variation for the currently used program. In other examples, the user may select a specific stimulation program or rate the effectiveness of a particular stimulation program from a list presented via a display of user interface 74. Alternatively, programmer 24 may transmit a signal to IMD 16 indicating that control module 50 should execute locally stored programs or therapy routines. In such a manner, control over the electrical stimulation may be distributed between IMD 16 and external programmer 24, or may reside in either one alone.

Patient 14 may also provide an input that requests a therapy via programmer 24. In this way, patient 14 may use programmer 24 to control when the electrical stimulation is delivered to treat one or more symptoms. Patient 14 may instead provide an input that requests that IMD 16 terminate stimulation therapy. For example, the therapy may be sufficient that voluntary voiding of bladder 12 is not possible. Alternatively, the patient 14 may request delivery of stimulation to aid voiding, e.g., by causing bladder contraction in the case of urinary retention. These examples may be considered "on demand" therapy in response to patient input.

Power source 78 delivers operating power to the components of programmer 24. Power source 78 may include a battery and a power generation circuit to produce the operating power. In some examples, the battery may be rechargeable to allow extended operation. Recharging may be accomplished by electrically coupling power source 78 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 78 may include circuitry to monitor power remaining within a battery. In this manner, user interface 74 may provide a current battery level indicator or low battery level indicator when the battery needs to be replaced or recharged. In some cases, power source 78 may be capable of estimating the remaining time of operation using the current battery.

Figure 4A:
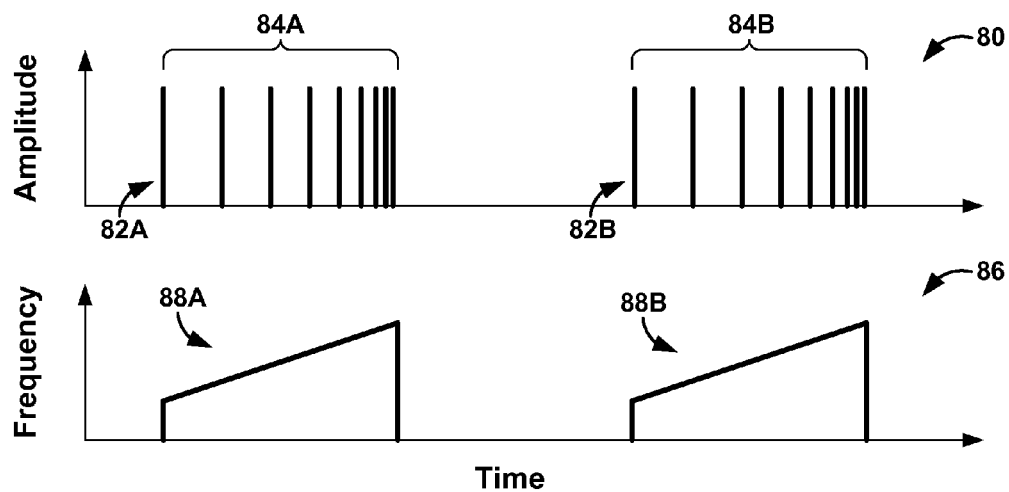
FIGS. 4A and 4B are example timing diagrams of linear pulse frequency variation within a burst of electrical stimulation pulses.
Figure 4B:
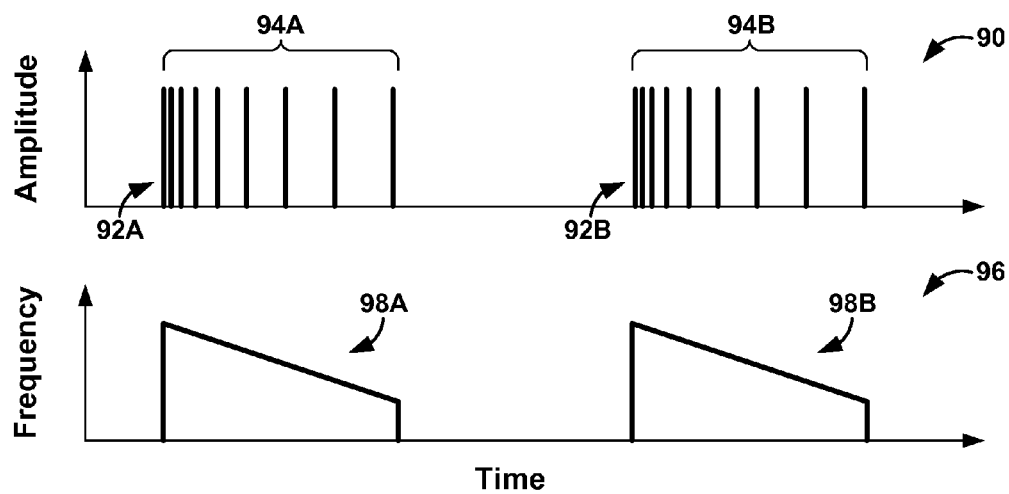

FIGS. 4A and 4B are example timing diagrams of linear pulse frequency variation within a burst of pulses. In general, frequency variation may be considered a change in the frequency of pulses in a burst such that the inter-pulse intervals between successive pulses changes. For example, if intra-burst pulse frequency increases over a period of time within the burst, then the inter-pulse interval decreases within that period of time. Similarly, if intra-burst pulse frequency decreases over a period of time within the burst, then the inter-pulse interval increases within that period of time. Hence, varying pulse frequency may be expressed in a variety of ways, e.g., in terms of pulse frequency or inter-pulse frequency. As one example, pulse frequency may be evaluated as an average pulse frequency for each given pulse taking into account preceding pulses leading up to that pulse. In this manner, if the pulse frequency is decreasing, the average pulse frequency will be decreasing for each successive pulse. The inverse is applicable in the case where pulse frequency is increasing. As an alternative, for an increasing pulse frequency, the average inter-pulse interval (time between successive pulses), taking into account preceding pules leading up to a given pulse, will decrease for each successive pulse. The inverse is applicable in the case where pulse frequency is decreasing. Hence, as examples, average pulse frequency or average inter-pulse interval, or other metrics, may be used to characterize pulse frequency as increasing or decreasing within a burst. In other examples, the change in intra-pulse frequency may be determined between consecutive pulses. At a minimum, the frequency change may be determined by the two intervals between three consecutive pulses. However, more than two inter-pulse intervals may be used to determine the intra-pulse frequency variation.

As shown in FIG. 4A, timing diagram 80 illustrates example bursts 84A and 84B (collectively "bursts 84") with respective pulses 82A and 82B (collectively "pulses 82") plotted over time. Bursts 84 are example bursts of pulses that may be delivered by IMD 16 during stimulation therapy. For example, burst 84A includes several electrical pulses 82A at a substantially similar amplitude over time. Pulses 82A would be an example of intra-burst pulses. Pulses 82A are not delivered at a constant pulse frequency (i.e., pulse rate) over the length of burst 84A. Instead, pulses 82A have a varying pulse frequency over the course of burst 84A. In some cases, pulse frequency may be fixed over some portion or portions of a burst and varying over one or more other portions of the burst. Alternatively, pulses may be vary over the entire course of a burst, e.g., from higher to lower frequency or lower to higher frequency. The burst patterns may be selected, in some examples, to mimic the properties of nerve firings, and may produce enhanced afferent signals to trigger bladder contractions.

Pulses 82A are shown in FIGS. 4A and 4B as being delivered closer and closer together, such that the pulse frequency is increasing over time. In particular, the inter-pulse interval between successive pulses 82A decreases over time within the burst. Pulses 82B of burst 84B are substantially similar to pulses 82A of burst 84B. Timing diagram 80 indicates timing of pulses 82 in a time domain, with pulse amplitude on the vertical axis and time on the horizontal axis. Timing diagram 86 illustrates the timing of pulses 82 in the frequency domain with frequency value on the vertical axis and time on the horizontal axis. Bursts 88A and 88B (collectively "bursts 88") illustrate that the frequency of pulses within each burst increases over time, and that bursts 88 have an intra-burst pulse frequency variation that is substantially equal, i.e., consistent. In the example of FIG. 4A, bursts 88 indicate that the frequency change may be characterized as a linear profile, e.g., pulses 82 are linearly varied over time. Even if some parameters of pulses 82 change over time, timing diagram 86 would still indicate a linear profile if the intra-burst pulse frequency variation was linear.

In any of the examples of FIGS. 4A, 4B, 5A, and 5B, the electrical pulses may vary between pulses or between bursts. FIG. 4A is used as an example illustration of these different variations. For example, the frequency variation of pulses 82A may be different from that of pulses 82B (e.g., an inter-burst pulse frequency variation). In another example, pulses 82A may have a different amplitude than pulses 82B, or the amplitude within pulses 82A may be dissimilar. It is noted that pulses 82 have a pulse width as well, but the pulse width is not shown in timing diagrams 80 or 86. Although the pulses are shown as narrow spikes for purposes of illustration, the pulses may have a variety of pulse widths. The pulse widths may be the same for each pulse in a burst or different for different pulses in a burst. In addition, bursts 84, including additional bursts not shown in FIG. 4A, may include a burst frequency and inter-burst interval that may vary during stimulation. This inter-burst frequency variation may be provided in addition to the intra-burst pulse frequency variation.

In the example of FIG. 4A, each of bursts 84 may last for a duration between approximately 1 second to 100 seconds. The intra-burst frequency may start at approximately 0.1 Hz and increase to approximately 90 Hz, or start at approximately 10 Hz and increase to approximately 60 Hz. However, the intra-burst frequency may vary within a smaller range, e.g., 20 Hz to 40 Hz, in other examples. The intra-burst frequency may change from pulse to pulse, in a step-wise function over two or more pulses or a period of time, or in a liner regression manner.

As shown in FIG. 4B, timing diagram 90 illustrates example bursts 94A and 94B (collectively "bursts 94") with respective pulses 92A and 92B (collectively "pulses 92") plotted over time. Bursts 94 are example bursts of pulses that may be delivered by IMD 16 during stimulation therapy. For example, burst 94A includes several electrical pulses 92A at a substantially similar amplitude over time. Pulses 92A are an example of intra-burst pulses. Pulses 92A are not delivered at a constant pulse frequency (i.e., pulse rate) over the length of burst 94A. Instead, pulses 92A have a varying pulse frequency over the course of burst 94A. Pulses 92A are shown as being delivered further and further away from each other, such that the pulse frequency is decreasing over time. In particular, the inter-pulse interval between successive pulses 82A increases over time within the burst. Pulses 92B of burst 94B are substantially similar to pulses 92A of burst 94B.

In the example of FIG. 4B, each of bursts 94 may last for a duration between approximately 1 second to 100 seconds. The intra-burst frequency may start at approximately 90 Hz and decrease to approximately 0.1 Hz, or start at approximately 60 Hz and decrease to approximately 10 Hz. However, the intra-burst frequency may vary within a smaller range, e.g., 20 Hz to 40 Hz, in other examples. The intra-burst frequency may change from pulse to pulse, in a step-wise function over two or more pulses or a period of time, or in a liner regression manner.

Timing diagram 96 illustrates the timing of pulses 92 in the frequency domain. Bursts 98A and 98B (collectively "bursts 98") illustrate that the frequency of pulses within each burst decreases over time, and that bursts 98 have an intra-burst pulse frequency variation that is substantially equal, i.e., consistent. Similar to bursts 88 of FIG. 4A, bursts 98 indicate that the frequency change may be characterized as a linear profile, e.g., pulses 92 are linearly varied over time. Even if some parameters of pulses 92 change over time, timing diagram 96 would still indicate a linear profile if the intra-burst pulse frequency variation was linear.

Figure 5A:
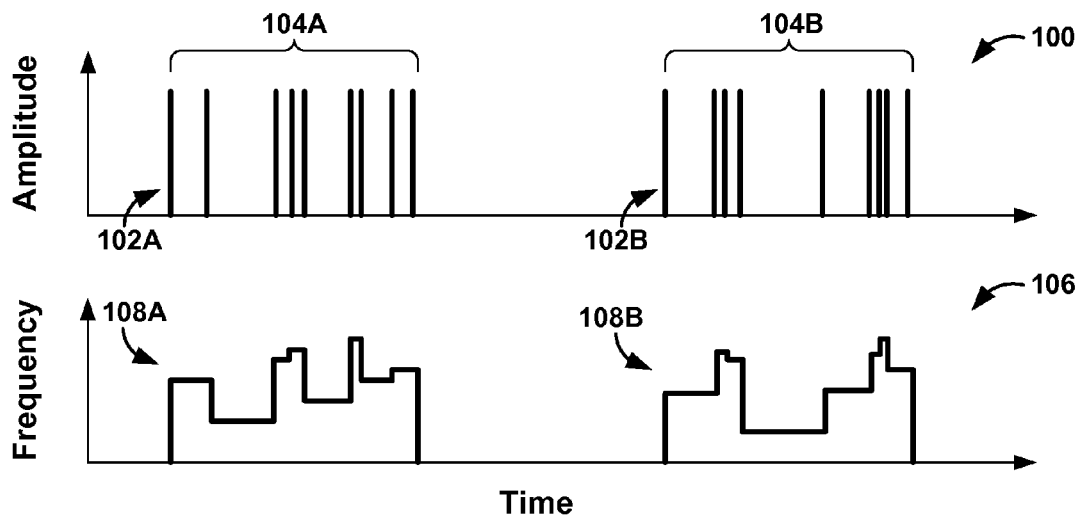
FIGS. 5A and 5B are example timing diagrams of random and polynomial pulse frequency variation within a burst of electrical stimulation pulses.
Figure 5B:
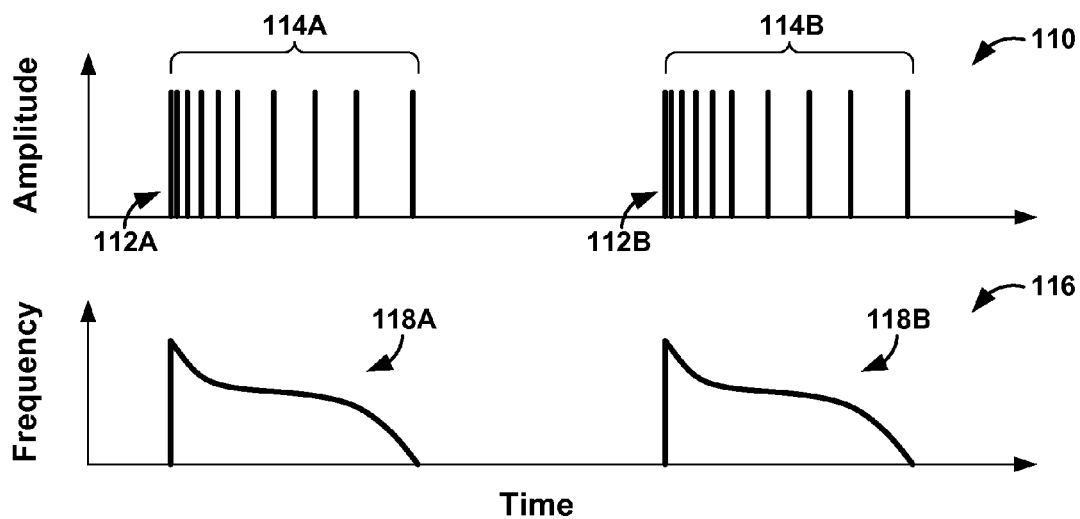

FIGS. 5A and 5B are example timing diagrams of random and polynomial pulse frequency variation within a burst of pulses. As shown in FIG. 5A, timing diagram 100 illustrates example bursts 104A and 104B (collectively "bursts 104") with respective pulses 102A and 102B (collectively "pulses 102") plotted over time. Bursts 104 are example bursts of pulses that may be delivered by IMD 16 during stimulation therapy. For example, burst 104A includes several electrical pulses 102A at a substantially similar amplitude over time. Pulses 102A would be another example of intra-burst pulses. Pulses 102A are not delivered at a constant pulse frequency (i.e., pulse rate) the length of burst 104A. Instead, pulses 102A have a varying pulse frequency over the course of burst 104A. In fact, the variation of pulses 102A is random within burst 104 over time. In other words, the intra-burst pulse frequency increases or decreases between pulses. In some examples, the intra-burst pulse frequency may be varied randomly or pseudo-randomly, e.g., with no intentional order. Pulses 102B of burst 104B are not similar in frequency to pulses 102A of burst 104B. However, other examples of random intra-burst pulse frequency variation may provide the same random frequency variation between bursts.

Timing diagram 106 illustrates the timing of pulses 102 in the frequency domain. Bursts 108A and 108B (collectively "bursts 108") illustrate that the frequency of pulses within each burst varies randomly over time, and that bursts 108 have an intra-burst pulse frequency variation that is not consistent between pulses. Further, the intra-burst pulse frequency variation changes between bursts 108A and 108B. Bursts 108 indicate that the frequency change may be characterized as a random profile, e.g., pulses 102 are randomly varied over time. The randomness of the intra-burst pulse frequency variation may be generated automatically by control module 50 using random frequency generation instructions stored in memory 56. Random variation may be useful to capture different nerve or muscle fibers, or prevent adaptation, for example. Even if some parameters of pulses 102 change over time, timing diagram 106 would still indicate a random profile if the intra-burst pulse frequency variation was random.

As shown in FIG. 5B, timing diagram 110 illustrates example bursts 114A and 114B (collectively "bursts 114") with respective pulses 112A and 112B (collectively "pulses 112") plotted over time. Bursts 114 are example bursts of pulses that may be delivered by IMD 16 during stimulation therapy. For example, burst 114A includes several electrical pulses 112A at a substantially similar amplitude over time. Pulses 112A would be an example of intra-burst pulses. Pulses 112A are not delivered at a constant pulse frequency (i.e., pulse rate) over the length of burst 114A. Instead, pulses 112A have a varying pulse frequency over the course of burst 114A. Pulses 112A are shown as being delivered further away from each other over time (i.e., having increasing inter-pulse intervals), such that the pulse frequency is generally decreasing over time. However, the pulse frequency is not decreasing at the same rate over time. Pulses 112B of burst 114B are substantially similar to pulses 112A of burst 114B.

Timing diagram 116 illustrates the timing of pulses 112 in the frequency domain. Bursts 118A and 118B (collectively "bursts 118") illustrate that the frequency of pulses within each burst generally decreases over time, but that the rate of decreasing frequency is not constant. Instead, bursts 118 indicate that the frequency change may be characterized as a polynomial profile, e.g., pulses 112 are varied in frequency over time based on a predetermined polynomial equation. In this manner, the clinician or control module 50 may create a curve fit that defines two or more changes in frequency variation within a single burst. The polynomial profile that defines the intra-burst pulse frequency variation may allow the frequency to be varied in any desired rate within each burst.

In an alternative example, the intra-burst pulse frequency variation may follow an exponential profile such that the pulse frequency is exponentially varied over time. In other words, exponentially varying the pulse frequency may result in an increasing or decreasing rate of frequency change. The various examples of intra-burst pulse frequency variation provided in FIGS. 4A, 4B, 5A, and 5B are merely examples of potential variations in pulse frequency. Any other types of frequency profiles or variations in intra-burst pulse frequency are also contemplated in this disclosure, including intra-burst pulse frequency variations derived from intrinsic nerve impulses as described in FIGS. 6A, 6B, and 6C.

In another alternative example, the intra-burst pulse frequency variation may be substantially zero. In other words, there may be no pulse frequency variation within each burst. In this example, the pulse frequency may still be between approximately 1 Hz and 100 Hz, or more specifically, between approximately 20 Hz and 40 Hz. Although the pulse amplitudes may also be substantially constant within the burst, the pulse amplitude may vary between pulses of a single burst.

Figure 6A:
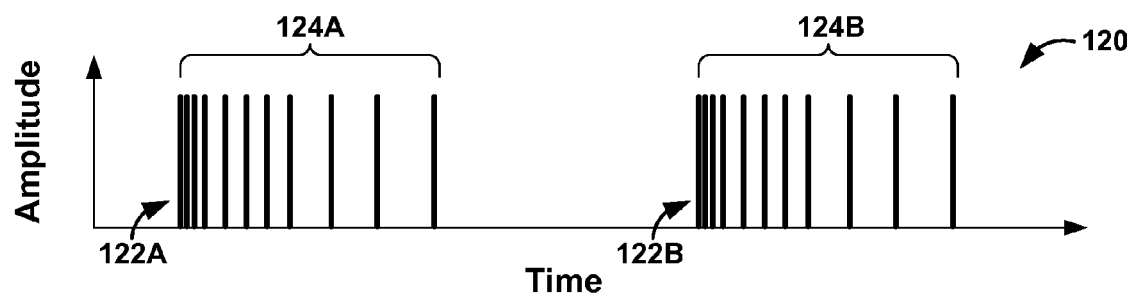
FIG. 6A is an example timing diagram of detected intrinsic nerve impulses over time.

FIG. 6A is an example timing diagram 120 of detected intrinsic nerve impulses 122A and 122B over time. As shown in FIG. 6A, timing diagram 120 illustrates example intrinsic nerve impulses 122A and 122B (collectively "impulses 122") of bursts 124B and 124A (collectively "bursts 124"), respectively. Intrinsic nerve impulses 122 are merely example impulses that may be observed in an animal or human. In the example of FIG. 6A, nerve impulses 122 are example impulses detected by impulse sensing module 53 of IMD 16. Although only pulse amplitude and pulse frequency is shown, impulses 122 also may be defined by a pulse width and burst frequency.

Intrinsic nerve impulses 122 are plotted over time to indicate the relative change in impulse frequency over time. Similar to the example of FIG. 5B, impulses 122A of burst 124 do not occur at a constant frequency (i.e., rate) over the length of burst 124A. Instead, impulses 122A have a varying frequency over the course of burst 124A. Impulses 122A are shown as being delivered further away from each other over time, such that the frequency is generally decreasing over time. However, the frequency is not decreasing at the same rate over time. Instead, impulses 122A, for example, are varied in frequency over time based on a polynomial equation. In other words, the curve or profile of the intra-burst impulse frequency variation may be defined using two or more different changes in frequency rate. Therefore, the intrinsic nerve impulse frequency variation of bursts 124 may be complex and require curve fitting or modeling to duplicate, which may be performed, e.g., in a DSP or other logic or signal analysis circuitry provided in an IMD (e.g., within control module 50), programmer or other computing device. Since bursts 124A and 124B include intrinsic nerve impulses, the intra-burst impulse frequency variation may not be identical between bursts 124.

After impulses 122, for example, are detected by impulse sensing module 53, the detected intra-burst impulse frequency variation may be stored in memory 56. In addition, memory 56 may store other parameters that define the detected nerve impulses. Based on the parameters from the detected intrinsic nerve impulses, control module 50 or a user may determine intra-burst pulse frequency variations that may provide therapy to patient 14. For example, control module 50 may define bursts with intra-burst pulse frequency variation profiles that generally mimic intrinsic nerve impulses, such as those sensed by impulse sensing module 52.

Figure 6B:
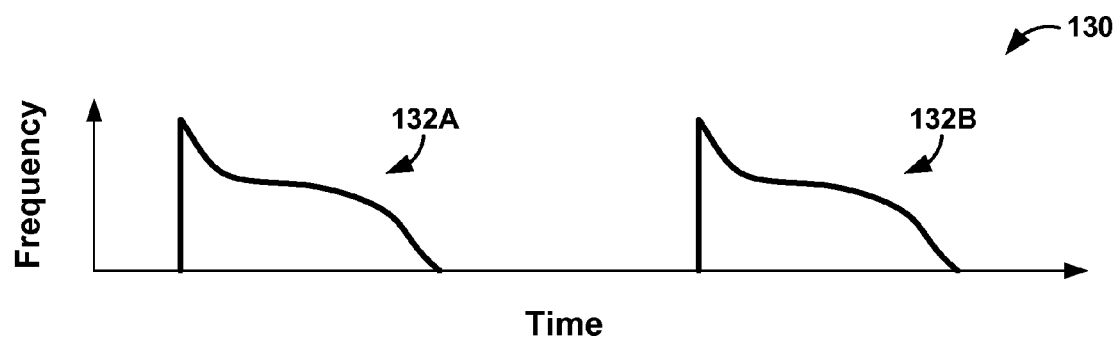
FIGS. 6B and 6C are example diagrams of pulse frequency variation based on detected intrinsic nerve impulse frequency variation.
Figure 6C:
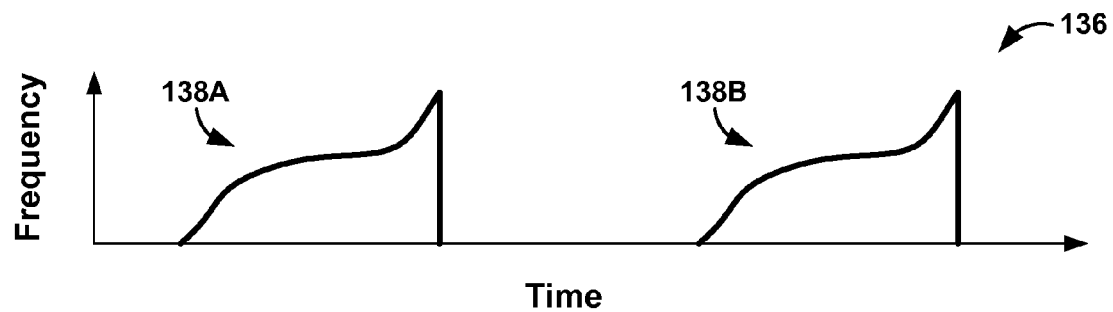

FIGS. 6B and 6C are example timing diagrams 130 and 136 of stimulation configured to provide bursts of pulses with pulse frequency variation based on detected intrinsic nerve impulse frequency variation. Timing diagrams 130 and 136 provide example intra-burst pulse frequency variations based on the intrinsic nerve impulses detected in FIG. 6A. As shown in FIG. 6B, timing diagram 130 may include bursts 132A and 132B (collectively "bursts 132") that include electrical stimulation pulses. The pulse frequency of delivered pulses within each of bursts 132 is plotted against time.

The frequency variation of generated stimulation bursts 132 may be determined calculated) to be similar to, or mimic, the intra-burst impulse frequency variation of pulses 122. In this manner, control module 50 may create a curve fit that substantially matches or approximates the detected pulse frequency variations within one or more of bursts 124. In one example, a stimulation burst 132 may have a same or similar number of pulses, with a same or similar arrangement of inter-pulse intervals and resulting pulse frequencies, as the pulses in a sensed nerve impulses. The frequency variation profile and other parameters may be determined based on a single burst or multiple bursts of nerve impulses. For multiple nerve impulses, an average or some other appropriate statistical measure of the characteristics of the impulses may be used to establish the parameters of the stimulation bursts. In other examples, the change in intra-pulse frequency may be determined between consecutive pulses. At a minimum, the frequency change may be determined by the two intervals between three consecutive pulses. However, more than two inter-pulse intervals may be used to determine the intra-pulse frequency variation. The curve fit may be an equation that creates a polynomial profile defining the intra-burst pulse frequency variation that simulates the detected nerve impulses. In this manner, the frequency variation of bursts 132 may be similar to any type of profile since the variation is based upon the detected intra-burst impulse frequency variation.

In other examples, bursts 132 may not be defined by a polynomial equation. Instead, each of bursts 132 may be defined by a sequential number of individual pulse frequencies. In other words, control module 50 may simply take the different detected impulse frequencies from burst 124A, for example, and generate a burst of pulses with the same detected frequencies. Therefore, the intra-burst pulse frequency variation of bursts 132 may be generated without any calculation or curve fit.

Generally, control module 50 may generate the intra-burst pulse frequency variation for multiple bursts 132 from the detected nerve impulses of only one burst 124A. In this manner, the detected impulse frequency may be a sample of the impulse bursts physiologically generated within the patient. In addition, using a sample of impulse bursts may result in bursts 132 having identical generated intra-burst pulse frequency variations. However, control module 50 may update the detected intra-burst impulse frequency periodically or upon the detection of an update event. This update event may indicate when changes to the detected intra-burst impulse frequency should be updated. In other examples, the impulse frequency variation may be continually updated such that stimulation therapy is closely matched to any changes in nerve activity.

Example update events may include the detection of a predetermined number of bursts of impulses, an expiration of a predetermined time period, an ineffective therapy, or a user request to update the determination of the frequency variation. In other words, control module 50 may identify an update event and then again detect the varying frequencies of the impulses. The update event may be time-based or therapy-based. For example, a predetermined time period may be 7 days such that control module 50 again detects the frequency variation of impulses to determine an updated intra-burst pulse frequency variation. In another example, if the detection of bladder contractions during stimulation indicates that the therapy is not effective, the control module 50 may attempt to adjust stimulation according to a newly detected intra-burst impulse frequency variation.

As shown in FIG. 6C, timing diagram 136 may include bursts 138A and 138B (collectively "bursts 138") that include electrical stimulation pulses. The pulse frequency of delivered pulses within each of bursts 132 is plotted against time. Bursts 138 may be substantially similar to bursts 132 of FIG. 69, and bursts 138 may even be calculated or determined similar to bursts 132. However, the intra-burst pulse frequency variation of bursts 138 may be determined as an inverse pulse frequency variation from the frequency variation detected from intrinsic nerve impulses (e.g., pulses 122A). An inverse pulse frequency variation may disrupt, neutralize, counteract or interfere with the intrinsic nerve impulses.

For example, once control module 50 determines the frequency variation of impulses 122A, as described with respect to FIG. 6B, control module 50 may invert the frequency variation such that the first detected frequencies of pulses 122A are the last frequencies of burst 138A. In other words, an inverse intra-burst pulse frequency variation may be an inverse of the intrinsic nerve impulse frequency variation with respect to time. An inverse frequency variation may be desirable to disrupt afferent nerve impulses, rather than mimic them. In this manner, instead of mimicking and possibly reinforcing nerve impulses, IMD 16 may generate burst of pulses that disrupt the nerve impulses, possibly alleviating dysfunction. As an example, disruption of nerve impulses using stimulation with an inverse frequency variation profile could be effective in quieting the bladder, e.g., possibly reducing bladder contraction frequency to alleviate bladder urgency or urge incontinence.

Figure 7:
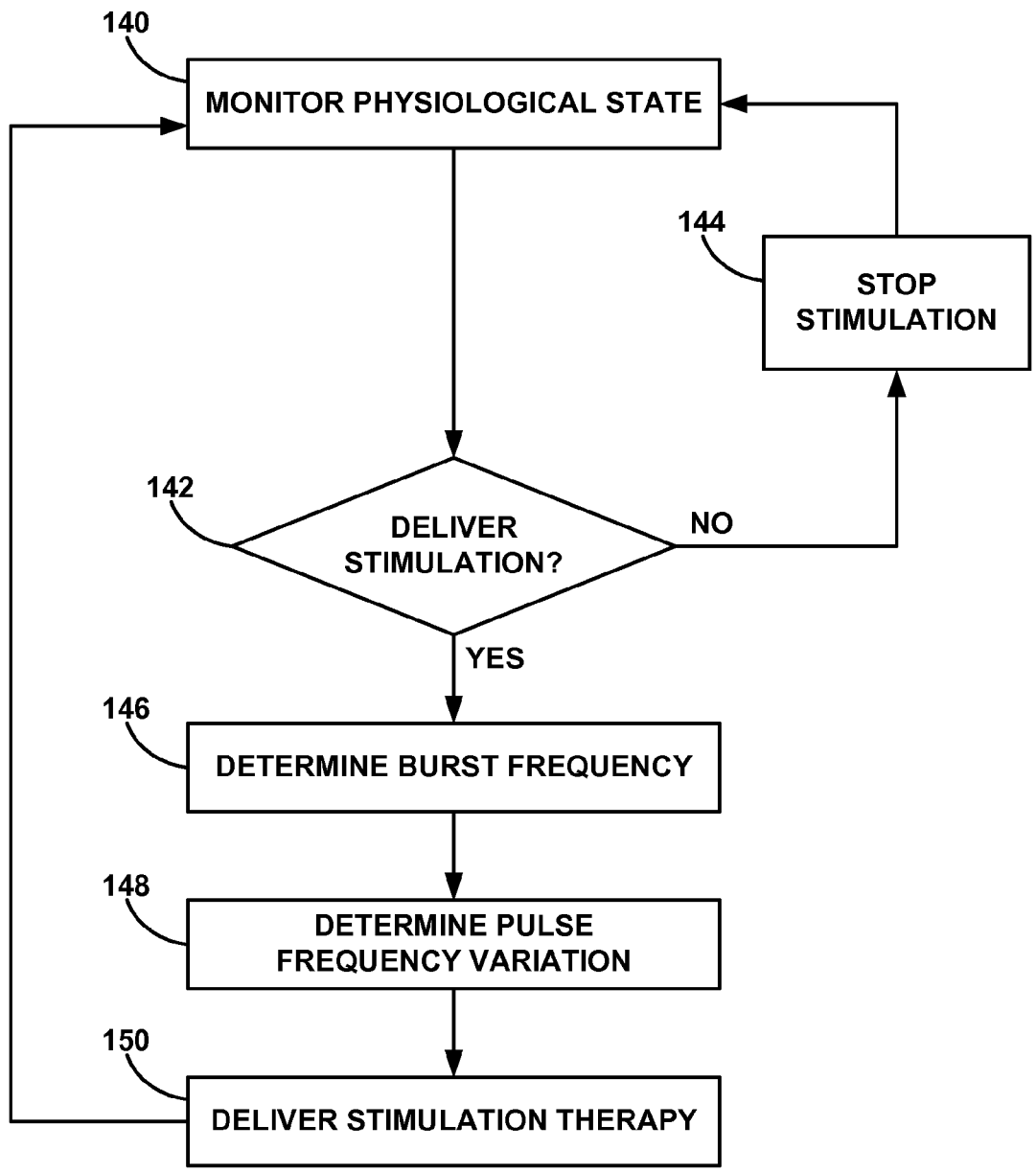
FIG. 7 is a flow diagram that illustrates an example technique for delivering electrical stimulation therapy with varying pulse frequencies within bursts of electrical stimulation pulses.

FIG. 7 is a flow diagram that illustrates an example technique for delivering electrical stimulation therapy with varying pulse frequencies within bursts of pulses. The technique of FIG. 7 is described with respect to control module 50 and therapy delivery module 52 of IMD 16. However, other devices, such as programmer 24 may also be involved in other examples (e.g., control module 70 of programmer 24 may perform some or all of the processes attributed to control module 50). As shown in FIG. 7, control module 50 monitors the physiological state of patient 14 to determine when to deliver stimulation therapy (140). As described herein, physiological state may be a bladder contraction frequency, a bladder pressure, a posture state, an activity state, or any other measureable indication that patient 14 may be need therapy. In other examples, where a physiological state is not used to determine when to deliver therapy, control module 50 may wait to receive a therapy request from programmer 24, wait for a timer to elapse, or wait for a specified therapy window associated with a time of day.

If stimulation therapy is not to be delivered ("NO" branch of block 142), control module 50 stops stimulation if it is being delivered (144) and continues to monitor the physiological state of patient 14 (140). If control module 50 detects that the physiological state indicates stimulation therapy should be delivered ("YES" branch of block 142), control module 50 determines the inter-burst frequency (146) and the intra-burst pulse frequency variation (148). These frequencies may be determined based on a selected therapy program or individually selected by a user, or selected to mimic or disrupt sensed nerve impulses. Example inter-burst frequencies may be between approximately 1 Hz and 10 Hz and example intra-burst pulse frequencies may be varied between 20 Hz and 40 Hz. Once the parameters of the stimulation therapy are determined, control module 50 directs therapy delivery module 52 to deliver the stimulation therapy (150). Control module 50 then continues to monitor the physiological state of patient 14 (140).

Figure 8:
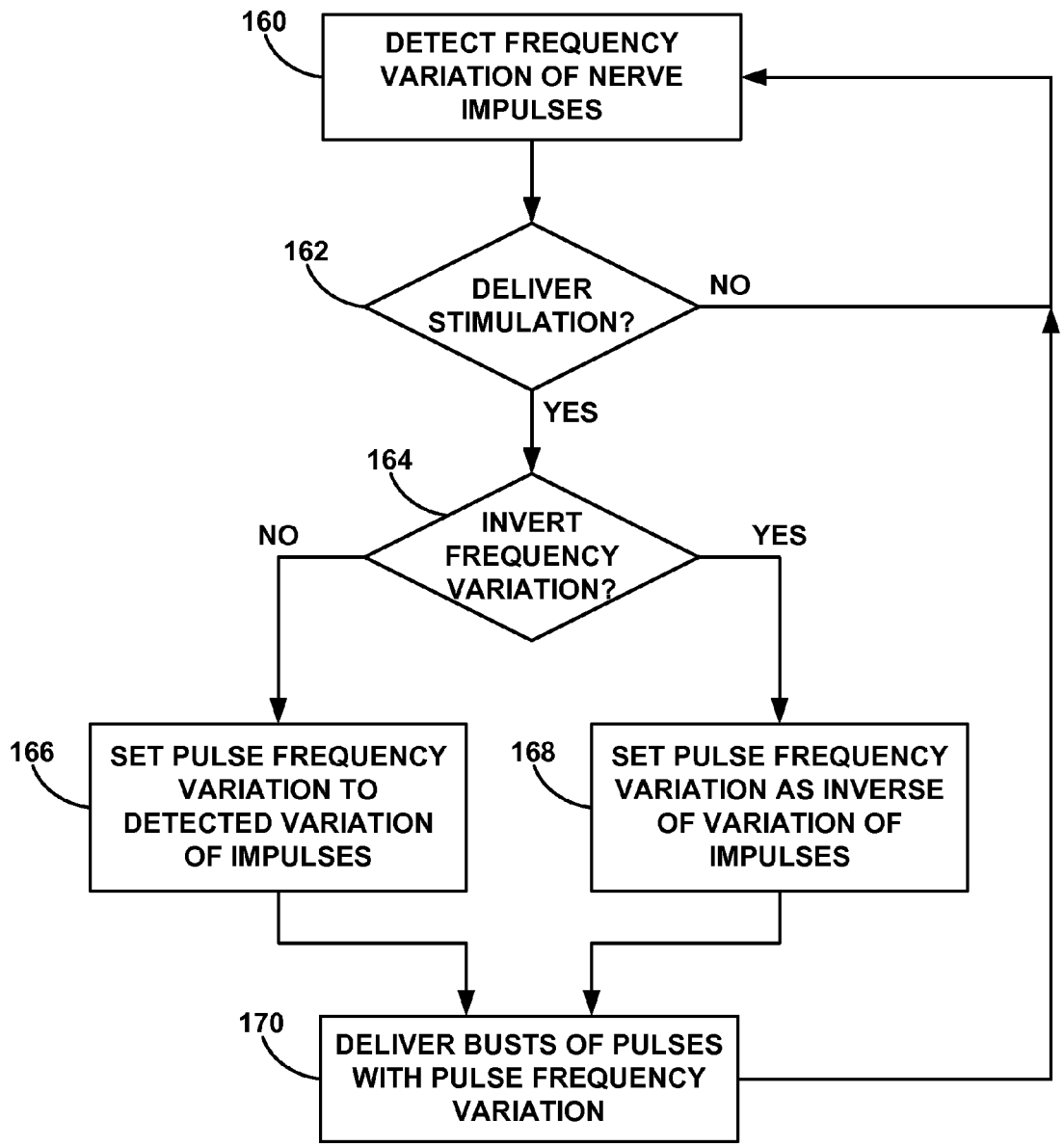
FIG. 8 is a flow diagram that illustrates an example technique for delivering electrical stimulation therapy with varying pulse frequencies based on detected nerve impulse frequency variation.

FIG. 8 is a flow diagram that illustrates an example technique for delivering electrical stimulation therapy with varying pulse frequencies based on detected nerve impulse frequency variation. The technique of FIG. 8 is described with respect to control module 50, therapy delivery module 52, and impulse sensing module of IMD 16. However, other devices, such as programmer 24 may also be involved in other examples (e.g., control module 70 of programmer 24 may perform some or all of the processes attributed to control module 50). As shown in FIG. 8, impulse sensing module 53 may detect the frequency variation of intrinsic nerve impulses (160). The nerve impulses may be detected for a patient, e.g., periodically or continuously by IMD 16. In other examples, the nerve impulses for a patient may be predetermined in clinic, or the nerve impulses or associated characteristics may be assumed based on data for a given patient population or based on expected nerve impulses. Impulse sensing module 53 may detect various parameters of the nerve impulses, e.g., pulse frequency, amplitude, pulse width, burst length, and burst frequency. If control module 50 is not to deliver stimulation ("NO" branch of block 162), impulse sensing module 53 may continue to detect impulse frequencies, e.g., in the case of impulses sensed from the patient.

If control module 50 is to deliver stimulation therapy ("YES" branch of block 162), control module 50 determines whether the detected intra-burst frequency variation is to be inverted (164). This determination may be controlled by previous selection of a particular therapy program. For example, an inverse intra-burst pulse frequency variation may be used to disrupt or interfere with the intrinsic nerve impulse. If the infra-burst pulse frequency variation is not to be inverted ("NO" branch of block 164), control module 50 sets the intra-burst pulse frequency variation to approximately mimic the detected impulse frequency variation (166). If the intra-burst pulse frequency variation should be inverted ("YES" branch of block 164), control module 50 sets the infra-burst pulse frequency variation as the inverse of the detected impulse frequency variation (168). Once the intra-burst pulse frequency variation is set by control module 50, control module 50 controls therapy delivery module 52 to deliver bursts of pulses with the set infra-burst pulse frequency variation (170). Subsequently, impulse sensing module 53 continues to detect the frequency variation of intrinsic nerve impulses (160).

In other examples, control module 50 may set the intra-burst pulse frequency variation to a variation, or variation profile, other than just the same as the detected impulse frequency variation or the inverse of the detected impulse frequency variation. For example, control module 50 may use the detected impulse frequency variation to generate any type of intra-burst pulse frequency variation that may be useful to treat patient 14.

This disclosure provides various techniques. In one example, a method may include delivering electrical stimulation therapy to a patient, wherein the electrical stimulation therapy comprises a plurality of bursts and a plurality of pulses within each of the plurality of bursts, and varying, by a control module, a pulse frequency of the plurality of pulses within each of the plurality of bursts, wherein the pulse frequency is varied between approximately 20 Hz and 40 Hz. Varying the pulse frequency may include one of increasing the pulse frequency within each of the plurality of bursts or decreasing the pulse frequency within each of the plurality of bursts. Varying the pulse frequency may also include at least one of linearly varying the pulse frequency, exponentially varying the pulse frequency, and polynomially varying the pulse frequency.

In some examples, varying the pulse frequency may include randomly varying the pulse frequency within each of the plurality of bursts. The burst frequency of the plurality of bursts may be between approximately 1 Hz and 10 Hz. The method may also include varying at least one of a current amplitude or a voltage amplitude of the plurality of pulses within each of the plurality of bursts. In other examples, the method may include detecting a physiological state of the patient, wherein varying the pulse frequency comprises one of increasing the pulse frequency, decreasing the pulse frequency, or randomly changing the pulse frequency based on the detection. The method may also include detecting a frequency variation of intrinsic nerve impulses, wherein varying the pulse frequency of the plurality of pulses comprises varying the pulse frequency according to one of the detected frequency variation or an inverse of the detected frequency variation. The electrical stimulation therapy may be configured to treat at least one of bladder dysfunction or colorectal dysfunction.

In another example, a system may include a therapy delivery module configured to generate and deliver electrical stimulation therapy to a patient, wherein the electrical stimulation therapy comprises a plurality of bursts and a plurality of pulses within each of the plurality of bursts, and a control module configured to vary a pulse frequency of the plurality of pulses within each of the plurality of bursts, wherein the pulse frequency is varied between approximately 20 Hz and 40 Hz. The control module may be configured to increase the pulse frequency within each of the plurality of bursts or decrease the pulse frequency within each of the plurality of bursts. In addition, the control module may be configured to at least one of linearly vary the pulse frequency, exponentially vary the pulse frequency, and polynomially vary the pulse frequency.

In some examples, the control module may be configured to randomly vary the pulse frequency within each of the plurality of bursts. The burst frequency of the plurality of bursts may be between approximately 1 Hz and 10 Hz. In some examples, the control module may be configured to vary at least one of a current amplitude or a voltage amplitude of the plurality of pulses within each of the plurality of bursts.

In other examples, the system may include a sensor configured to detect a physiological state of the patient, wherein the control module is configured to one of increase the pulse frequency, decrease the pulse frequency, or randomly vary the pulse frequency based on the detection. The system may also include an impulse sensing module configured to detect a frequency variation of intrinsic nerve impulses, wherein the control module is configured to vary the pulse frequency according to one of the detected frequency variation or an inverse of the detected frequency variation.

The electrical stimulation therapy may be configured to treat at least one of bladder dysfunction or colorectal dysfunction. The control module and therapy delivery module may be both housed within an implantable medical device. The therapy delivery module may be housed within an implantable medical device and the control module may be housed within an external programmer.

In another examples, a system may include means for delivering electrical stimulation therapy to a patient, wherein the electrical stimulation therapy comprises a plurality of bursts and a plurality of pulses within each of the plurality of bursts, and means for varying a pulse frequency of the plurality of pulses within each of the plurality of bursts, wherein the pulse frequency is varied between approximately 20 Hz and 40 Hz. The means for varying the pulse frequency may at least one of linearly vary the pulse frequency, exponentially vary the pulse frequency, and polynomially vary the pulse frequency.

The system may also include means for detecting a physiological state of the patient, wherein the means for varying the pulse frequency one of increases the pulse frequency, decreases the pulse frequency, or randomly varies the pulse frequency based on the detection. The system may, in other examples, include means for detecting a frequency variation of intrinsic nerve impulses, wherein the means for varying the pulse frequency varies the pulse frequency according to one of the detected frequency variation or an inverse of the detected frequency variation.

In one example, a method may include detecting, by a first processor (e.g., an impulse sensing module), a frequency variation of intrinsic nerve impulses within a burst of impulses, determining, by a second processor (e.g., a control module), an inverse pulse frequency variation based on the frequency variation of intrinsic nerve impulses, and delivering electrical stimulation therapy to a patient, wherein the electrical stimulation therapy comprises one or more bursts of pulses at least partially defined by the inverse pulse frequency variation. The inverse pulse frequency variation may include pulse frequencies varied between approximately 20 Hz and 40 Hz. The method may also include updating the determination in response to detecting one of a predetermined number of bursts of impulses, an expiration of a predetermined time period, an ineffective therapy, or a user request to update the determination.

The inverse pulse frequency variation may include one of increasing the pulse frequency within each of the plurality of bursts or decreasing the pulse frequency within each of the plurality of bursts. The inverse pulse frequency variation may also include at least one of linearly varying the pulse frequency, exponentially varying the pulse frequency, and polynomially varying the pulse frequency. The one or more bursts of pulses may be at least partially defined by a burst frequency between approximately 1 Hz and 10 Hz. The method may also include varying at least one of a current amplitude or a voltage amplitude of pulses within each of the one or more bursts of pulses.

The method may also include detecting a physiological state of the patient and one of beginning the delivery of electrical stimulation therapy or stopping the delivery of electrical stimulation therapy based on the detection. The electrical stimulation therapy may be configured to treat at least one of bladder dysfunction or colorectal dysfunction.

In another example, a system may include an impulse sensing module configured to detect a frequency variation of intrinsic nerve impulses within a burst of impulses, a control module configured to determine an inverse pulse frequency variation based on the frequency variation of intrinsic nerve impulses, and a therapy delivery module configured to deliver electrical stimulation therapy to a patient, wherein the control module at least partially defines one or more bursts of pulses of the electrical stimulation therapy by the inverse pulse frequency variation. The inverse pulse frequency variation may include pulse frequencies varied between approximately 20 Hz and 40 Hz.

The control module may be configured to update the determination in response to detecting one of a predetermined number of bursts of impulses, an expiration of a predetermined time period, an ineffective therapy, or a user request to update the determination. The control module may be configured to one of increase the pulse frequency within each of the plurality of bursts or decrease the pulse frequency within each of the plurality of bursts. The control module may also be configured to at least one of linearly vary the pulse frequency, exponentially vary the pulse frequency, and polynomially vary the pulse frequency.

The one or more bursts of pulses may be at least partially defined by a burst frequency between approximately 1 Hz and 10 Hz. The control module may be configured to vary at least one of a current amplitude or a voltage amplitude of pulses within each of the one or more bursts of pulses. The system may also include a sensor configured to detect a physiological state of the patient, wherein the control module is configured begin the delivery of electrical stimulation therapy or stop the delivery of electrical stimulation therapy based on the detection. In some examples, the electrical stimulation therapy may be configured to treat at least one of bladder dysfunction or colorectal dysfunction.

In an alternative example, a system may include means for detecting a frequency variation of intrinsic nerve impulses within a burst of impulses, means for determining an inverse pulse frequency variation based on the frequency variation of intrinsic nerve impulses, and means for delivering electrical stimulation therapy to a patient, wherein the electrical stimulation therapy comprises one or more bursts of pulses at least partially defined by the inverse pulse frequency variation. The inverse pulse frequency variation may include pulse frequencies varied between approximately 20 Hz and 40 Hz. The inverse pulse frequency variation may include at least one of linearly varying the pulse frequency, exponentially varying the pulse frequency, and polynomially varying the pulse frequency. The one or more bursts of pulses may be at least partially defined by a burst frequency between approximately 1 Hz and 10 Hz.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. White the techniques described herein are primarily described as being performed by control module 50 of IMD 16 and/or control module 70 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various embodiments have been described. These and other examples are within the scope of the following claims.

What is claimed is:

1. A method comprising:
   delivering electrical stimulation therapy to a patient, wherein the electrical stimulation therapy comprises a plurality of bursts and a plurality of pulses within each burst of the plurality of bursts; and
   varying, by a control module and within each burst of the plurality of bursts, a pulse frequency of the respective plurality of pulses within each burst of the plurality of bursts, wherein the pulse frequency is varied between approximately 20 Hz and 40 Hz.

2. The method of claim 1, wherein varying the pulse frequency comprises controlling the pulse frequency to vary by one of increasing, without decreasing, the pulse frequency within each burst of the plurality of bursts or decreasing, without increasing, the pulse frequency within each burst of the plurality of bursts.

3. The method of claim 2, wherein varying the pulse frequency within each burst comprises controlling the pulse frequency to vary by at least one of linearly varying the pulse frequency within each burst, exponentially varying the pulse frequency within each burst, or polynomially varying the pulse frequency within each burst.

4. The method of claim 1, wherein varying the pulse frequency comprises randomly varying the pulse frequency within each burst of the plurality of bursts.

5. The method of claim 1, wherein a burst frequency of the plurality of bursts is between approximately 1 Hz and 10 Hz.

6. The method of claim 1, further comprising varying, within each burst of the plurality of bursts, at least one of a current amplitude or a voltage amplitude of the respective plurality of pulses within each burst of the plurality of bursts.

7. The method of claim 1, further comprising detecting a physiological state of the patient, wherein varying the pulse frequency within each burst comprises one of increasing the pulse frequency within each burst, decreasing the pulse frequency within each burst, or randomly changing the pulse frequency within each burst based on the detection.

8. The method of claim 1, further comprising detecting a frequency variation of intrinsic nerve impulses, wherein varying the pulse frequency of the respective plurality of pulses within each burst comprises varying the pulse frequency within each burst according to one of the detected frequency variation or an inverse of the detected frequency variation.

9. The method of claim 1, wherein the electrical stimulation therapy is configured to treat at least one of bladder dysfunction or colorectal dysfunction.

10. The system of claim 1, wherein the electrical stimulation therapy is configured to treat at least one of bladder dysfunction or colorectal dysfunction.

11. The system of claim 1, wherein the control module and therapy delivery module are both housed within an implantable medical device.

12. The system of claim 1, wherein the therapy delivery module is housed within an implantable medical device, and wherein the control module is housed within an external programmer.

13. The method of claim 1, wherein delivering electrical stimulation therapy to the patient comprises delivering the electrical stimulation therapy at the varied pulse frequency to one or more spinal nerves of the patient.

14. The method of claim 1, wherein delivering electrical stimulation therapy to the patient comprises delivering the electrical stimulation therapy at the varied pulse frequency to one or more sacral nerves of the patient.

15. The method of claim 1, wherein varying the pulse frequency of the respective plurality of pulses within each burst comprises varying the pulse frequency to capture at least one of a plurality of different nerve fibers or a plurality of different muscle fibers within each burst of pulses.

16. The method of claim 1, further comprising detecting a frequency variation of intrinsic nerve impulses, wherein varying the pulse frequency of the respective plurality of pulses within each burst comprises varying the pulse frequency within each burst according to an inverse of the detected frequency variation.

17. The method of claim 1, wherein one or more parameters of the electrical stimulation therapy are selected to decrease a frequency of bladder contractions.

18. A system comprising:
a therapy delivery module configured to generate and deliver electrical stimulation therapy to a patient, wherein the electrical stimulation therapy comprises a plurality of bursts and a plurality of pulses within each burst of the plurality of bursts; and
a control module configured to vary, within each burst of the plurality of bursts, a pulse frequency of the respective plurality of pulses within each burst of the plurality of bursts, wherein the pulse frequency is varied between approximately 20 Hz and 40 Hz.

19. The system of claim 18, wherein the control module is configured to vary the pulse frequency by increasing, without decreasing, the pulse frequency within each burst of the plurality of bursts or decreasing, without increasing, the pulse frequency within each burst of the plurality of bursts.

20. The system of claim 19, wherein the control module is configured to vary the pulse frequency by at least one of linearly varying the pulse frequency within each burst, exponentially varying the pulse frequency within each burst, or polynomially varying the pulse frequency within each burst.

21. The system of claim 18, wherein the control module is configured to randomly vary the pulse frequency within each burst of the plurality of bursts.

22. The system of claim 18, wherein a burst frequency of the plurality of bursts is between approximately 1 Hz and 10 Hz.

23. The system of claim 18, wherein the control module is configured to vary, within each burst of the plurality of bursts, at least one of a current amplitude or a voltage amplitude of the respective plurality of pulses within each burst of the plurality of bursts.

24. The system of claim 18, further comprising a sensor configured to detect a physiological state of the patient, wherein the control module is configured to one of increase the pulse frequency within each burst, decrease the pulse frequency within each burst, or randomly vary the pulse frequency within each burst based on the detection.

25. The system of claim 18, further comprising an impulse sensing module configured to detect a frequency variation of intrinsic nerve impulses, wherein the control module is configured to vary the pulse frequency within each burst according to one of the detected frequency variation or an inverse of the detected frequency variation.

26. A system comprising:
means for delivering electrical stimulation therapy to a patient, wherein the electrical stimulation therapy comprises a plurality of bursts and a plurality of pulses within each burst of the plurality of bursts; and
means for varying, within each burst of the plurality of bursts, a pulse frequency of the respective plurality of pulses within each burst of the plurality of bursts, wherein the pulse frequency is varied between approximately 20 Hz and 40 Hz.

27. The system of claim 26, wherein the means for varying the pulse frequency at least one of linearly varies the pulse frequency within each burst, exponentially varies the pulse frequency within each burst, or polynomially varies the pulse frequency within each burst.

28. The system of claim 26, further comprising means for detecting a physiological state of the patient, wherein the means for varying the pulse frequency one of increases the pulse frequency within each burst, decreases the pulse frequency within each burst, or randomly varies the pulse frequency within each burst based on the detection.

29. The system of claim 26, further comprising means for detecting a frequency variation of intrinsic nerve impulses, wherein the means for varying the pulse frequency varies the pulse frequency within each burst according to one of the detected frequency variation or an inverse of the detected frequency variation.

* * * * *